(12) United States Patent
Leonetti et al.

(10) Patent No.: US 9,816,072 B2
(45) Date of Patent: Nov. 14, 2017

(54) METHOD FOR OBTAINING ANTIGEN-SPECIFIC HUMAN ANTIBODIES BY IN VITRO IMMUNISATION

(71) Applicant: COMMISSARIAT A L'ENERGIE ATOMIQUE ET AUX ENERGIES ALTERNATIVES, Paris (FR)

(72) Inventors: Michel Leonetti, Nozay (FR); Patricia Lamourette, Gif sur Yvette (FR); Herve Volland, Orsay (FR); Alexandra Savatier, Etampes (FR); Anne Wijkhuisen, Etampes (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/647,151

(22) PCT Filed: Nov. 26, 2013

(86) PCT No.: PCT/IB2013/060413
§ 371 (c)(1),
(2) Date: May 26, 2015

(87) PCT Pub. No.: WO2014/083499
PCT Pub. Date: Jun. 5, 2014

(65) Prior Publication Data
US 2015/0299655 A1  Oct. 22, 2015

(30) Foreign Application Priority Data

Nov. 27, 2012 (FR) .................................... 12 61315

(51) Int. Cl.
*A61K 39/39* (2006.01)
*C12N 5/078* (2010.01)
*A61K 39/00* (2006.01)

(52) U.S. Cl.
CPC ............ *C12N 5/0634* (2013.01); *A61K 39/39* (2013.01); *A61K 2039/575* (2013.01)

(58) Field of Classification Search
None
See application file for complete search history.

(56) References Cited

FOREIGN PATENT DOCUMENTS

WO     2011/092675 A2     8/2011

OTHER PUBLICATIONS

Kerscher et al., International Immunology, 25(5): 271-277. (2013).*

* cited by examiner

*Primary Examiner* — Nicole Kinsey White
(74) *Attorney, Agent, or Firm* — Arrigo, Lee & Guttman LLP

(57) ABSTRACT

A method for the in vitro immunization of human B lymphocytes, comprising culturing a total mononuclear cell population of human peripheral blood in the presence of an antigenic composition comprising at least one antigen covalently bonded to both: (i) a Tat protein or a Tat fragment capable of oligomerization and (ii) a ligand of a surface molecule specific to the antigen presenting cells; a method for producing antigen-specific human antibodies derived from said in vitro immunization method.

14 Claims, 14 Drawing Sheets

SEQUENCE LISTING

<160> NUMBER OF SEQ ID NOS: 9

<210> SEQ ID NO 1
<211> LENGTH: 116
<212> TYPE: PRT
<213> ORGANISM: artificial sequence
<220> FEATURE:

<223> OTHER INFORMATION: synthetic polypeptide

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala Asp Asn Lys Phe Asn
50                  55                  60

Lys Glu Gln Gln Asn Ala Phe Tyr Glu Ile Leu His Leu Pro Asn Leu
65                  70                  75                  80

Asn Glu Glu Gln Arg Asn Gly Phe Ile Gln Ser Leu Lys Asp Asp Pro
                85                  90                  95

Ser Gln Ser Ala Asn Leu Leu Ala Glu Ala Lys Lys Leu Asn Asp Ala
            100                 105                 110

Gln Ala Pro Lys
        115

<210> SEQ ID NO 2
<211> LENGTH: 116
<212> TYPE: PRT
<213> ORGANISM: artificial sequence
<220> FEATURE:
<223> OTHER INFORMATION: synthetic polypeptide

<400> SEQUENCE: 2

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Val Asp Asn Lys Phe Asn
50                  55                  60

Lys Glu Gln Gln Asn Ala Phe Tyr Glu Ile Leu His Leu Pro Asn Leu
65                  70                  75                  80

Asn Glu Glu Gln Arg Asn Ala Phe Ile Gln Ser Leu Lys Asp Asp Pro
                85                  90                  95

Ser Gln Ser Ala Asn Leu Leu Ala Glu Ala Lys Lys Leu Asn Asp Ala
            100                 105                 110

Gln Ala Pro Lys
        115

<210> SEQ ID NO 3
<211> LENGTH: 101
<212> TYPE: PRT
<213> ORGANISM: artificial sequence
<220> FEATURE:
<223> OTHER INFORMATION: synthetic polypeptide

<400> SEQUENCE: 3

Met Glu Pro Val Asp Pro Lys Leu Glu Pro Trp Lys His Pro Gly Ser
1               5                   10                  15

Gln Pro Lys Thr Ala Cys Asn Asn Cys Tyr Cys Lys Lys Cys Cys Phe
            20                  25                  30

His Cys Gln Val Cys Phe Thr Lys Lys Gly Leu Gly Ile Ser Tyr Gly

```
                  35                  40                  45
Arg Lys Lys Arg Arg Gln Arg Arg Ala Pro Gln Asp Ser Gln Thr
 50                  55                  60

His Gln Val Ser Leu Ser Lys Gln Pro Ala Ser Gln Pro Arg Gly Asp
 65                  70                  75                  80

Pro Thr Gly Pro Lys Glu Ser Lys Lys Lys Val Glu Arg Glu Thr Glu
                 85                  90                  95

Thr Asp Pro Val Asp
        100
```

<210> SEQ ID NO 4
<211> LENGTH: 318
<212> TYPE: DNA
<213> ORGANISM: artificial sequence
<220> FEATURE:
<223> OTHER INFORMATION: synthetic polynucleotide

<400> SEQUENCE: 4

```
ggtacccatg agccagtag atccgaaact ggagccctgg aagcatccag gtagccagcc      60
taagactgct tgtaacaact gctattgtaa aaagtgttgc tttcactgcc aggtttgttt    120
caccaaaaaa ggcctgggca tctcctatgg ccgcaagaag cgccgtcagc gccgccgtgc    180
tccgcaggac agccagactc accaggtttc tctgtccaag cagccggcat cccagccccg    240
cggtgacccg actggcccga aggaatccaa gaagaaggtg gagcgcgaga ccgagactga    300
tccggtggat taggatcc                                                 318
```

<210> SEQ ID NO 5
<211> LENGTH: 124
<212> TYPE: DNA
<213> ORGANISM: Artificial sequence
<220> FEATURE:
<223> OTHER INFORMATION: Synthetic polynucleotide

<400> SEQUENCE: 5

```
ggtacccagc aataattcct atagcaaaaa aagcagcttt catagccagg tgagctttac      60
caaaaaaggc ctgggcatta gctatggccg taaaaaacgt cgtcagcgtc gtcgttaagg    120
atcc                                                                124
```

<210> SEQ ID NO 6
<211> LENGTH: 124
<212> TYPE: DNA
<213> ORGANISM: Artificial sequence
<220> FEATURE:
<223> OTHER INFORMATION: Synthetic polynucleotide

<400> SEQUENCE: 6

```
ggtacccagc aataattcct atagcaaaaa aagcagcttt catagccagg tgagctttac      60
caaaaaaggc ctgggcatta gctatggccg taaaaaacgt cgtcagcgtc gtcgttaagg    120
atcc                                                                124
```

<210> SEQ ID NO 7
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 7

```
tcgtcgtttt gtcgttttgt cgtt                                           24
```

<210> SEQ ID NO 8
<211> LENGTH: 44
<212> TYPE: PRT
<213> ORGANISM: artificial sequence
<220> FEATURE:
<223> OTHER INFORMATION: synthetic peptide

<400> SEQUENCE: 8

Ser Leu Leu Met Trp Ile Thr Gln Cys Phe Leu Pro Val Ala Arg Gly
1               5                   10                  15

Pro Glu Ser Arg Leu Leu Glu Phe Tyr Leu Ala Met Pro Phe Ala Thr
            20                  25                  30

Pro Met Glu Ala Glu Leu Ala Arg Arg Ser Leu Ala
            35                  40

<210> SEQ ID NO 9
<211> LENGTH: 129
<212> TYPE: DNA
<213> ORGANISM: artificial sequence
<220> FEATURE:
<223> OTHER INFORMATION: synthetic polynucleotide

<400> SEQUENCE: 9
ctgctgatgt ggattaccca gtgctttctg ccggtggctc gtggcccgga aagccgtctg     60
ctggaatttt acctggcgat gccgtttgcg accccgatgg aagcggaact ggcgcgtcgt    120
agcctggcg                                                            129

METHOD FOR OBTAINING ANTIGEN-SPECIFIC HUMAN ANTIBODIES BY IN VITRO IMMUNISATION

Figure 1:
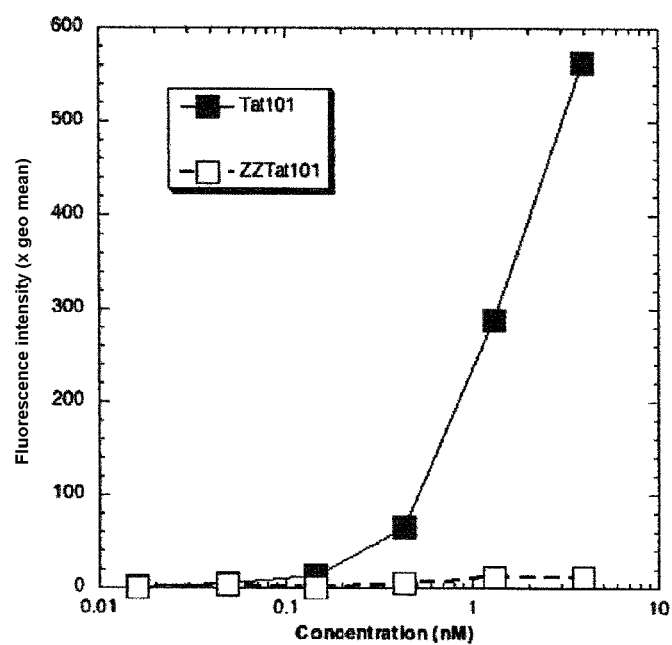

The present invention relates to a method for the in vitro immunization of human B lymphocytes using a total population of human peripheral blood mononuclear cells, which makes it possible to induce the production of human antibodies in vitro, more particularly of type G immunoglobulins (IgG) specific for an antigen (Ag). The present invention also relates to a method for producing antigen-specific human antibodies which is derived from said in vitro immunization method.

The obtaining of antigen-specific antibodies (Abs), and more particularly, IgGs, constitutes a major line of research in the therapeutic field which follows from the demonstration of clinical benefits obtained with respect to several diseases using IgGs specific for self proteins or proteins derived from pathogenic agents (Reichert, J. M., mAbs, 2011, 76-99).

In order to retain good therapeutic efficacy and to limit the risks of inappropriate side reaction, medicament antibodies must not trigger the reaction of the immune system of patients. It is for this reason that research groups seek to obtain human antibodies that will be likened to self proteins by the treated individuals and will, as a result, be tolerated by their immune system.

It is established that the T-dependent humoral immune response depends on the collaboration of three cell partners: dendritic cells (DCs), B lymphocytes and CD4+ T lymphocytes termed T-helper (Th) lymphocytes. The immune response initiation phase is located in the DC which is a specialized presenting cell (APC for Antigen Presenting Cell). During this phase, the DC ingests the exogenously provided antigen and certain antigenic fragments bind to the molecules of the class II major histocompatibility complex (MHC); the peptide/MHC molecule complexes are then trafficked to the surface of the DC. These complexes are then recognized by the receptors specifically expressed at the surface of the Th lymphocytes which thus become activated and contribute to the immune response. The B lymphocyte for its part, recognizes the extracellular antigen by means of the immunoglobulin expressed at its surface and thus internalizes it more efficiently (Lanzavecchia A., Nature, 1985, 314, 537-539). The B lymphocyte then behaves like an APC. It processes the internalized antigen in its endocytotic vesicules, the antigen fragments then bind to the molecules of the class II major histocompatibility complex (MHC) and then the peptide/MHC complexes are presented to the Th lymphocytes. The Th lymphocytes will, in turn, help the B lymphocyte to proliferate and to differentiate into an antibody-secreting plasmocytic cell and will play an essential role in isotype switching enabling the expression of antibodies of IgG class. During this process, several cytokines may contribute to the switching, in particular IL-21 and IL-4 (Pène et al., J. Immunol., 2004, 172, 5154-5157; Avery et al., J. Immunol., 2008, 181, 1767-1779).

The humoral immune response can also be triggered in a "T-independent" manner. This T-independent pathway is observed with antigens that exhibit repeated epitope motifs. Antigens bearing repeated motifs will be recognized at the surface of the B lymphocyte by several immunoglobulins which will assemble and thus contribute to setting up an activation signal sufficient for the cell to secrete the antibodies. The antibodies produced are principally IgMs since isotype switching is, usually, ineffective in the absence of help from Th lymphocytes.

Three approaches are generally used to generate human antibodies (Lanzavecchia et al., Current Opinion in Biotechnology, 2007, 18, 523-528). Two of them are based on the isolation of antibody-secreting specific B lymphocytes obtained from cell sources derived from individuals with immunity against the Ag of interest. The first approach, called Hu-Mouse-imm, uses, as cell source, samples from mice carrying human immunoglobulin loci (called Hu-Mice) which are vaccinated or infected with a pathogenic agent. The second approach, called Hu-imm, uses, as cell source, samples from humans with immunity against the Ag of interest. The third approach, called Ab-display, is based on the selection of antibodies from libraries of antibodies expressed on phages or on yeasts. These three pathways which have produced various results each have advantages but also limits. Thus, the Hu-imm approach proves to be suitable when it is desired to obtain IgGs specific for a pathogenic foreign agent which commonly infects humans. It is, on the other hand, unsuitable when the objective is to obtain antibodies against self antigens, such as cytokines or molecules expressed at the surface of cells, since these antigens are generally tolerated by the human immune system so as not to trigger an autoimmune reaction. Furthermore, for pathogenic agents which rarely affect humans, such as bioterrorism toxins, this approach proves difficult to apply owing to the small number of human individuals with immunity against these antigens. The Hu-Mouse-imm approach is, for its part, very suitable for inducing IgG responses against human self antigens. It is, on the other hand, unsuitable for pathogenic agents which cannot infect mice, such as the human immunodeficiency virus, the hepatitis C virus, the hepatitis B virus or the cytomegalovirus. Furthermore, the immune response induced in these mice is often suboptimal, probably due to the inconsistency between human IgGs and mouse Fc receptors. The Ab-display approach can, for its part, result in the isolation of human antibodies against a large variety of antigens. However, this approach requires a priori knowledge of the antigenic target since the selection principle is based on binding to a purified antigen and not on a functional test. This selection constraint results in the exclusion of viral neutralization tests and does not therefore make it possible to identify new neutralizing targets for complex pathogens. Furthermore, antibodies isolated in bacteria or yeasts may exhibit expression difficulties in mammalian cells.

The limits encountered in the three approaches described above have resulted in a search for alternative approaches based on the in vitro immunization of human B lymphocytes, in particular using a total population of human peripheral blood mononuclear cells (PBMCs) obtained from donors who are naïve with respect to the chosen therapeutic target, because human PBMCs constitute a renewable and readily accessible source of human B lymphocytes.

Compared with the Hu-imm and Hu-Mouse-imm approaches described previously, this approach has the advantage of not requiring individuals vaccinated against or infected with a pathogenic agent. Furthermore, compared with the Hu-Mouse-imm approach, it does not require a prior step of in vivo immunization and makes it possible to do without the animal.

Despite all the efforts made, the production of human antibodies by in vitro immunization technology using human peripheral blood mononuclear cells (PBMCs) obtained from donors who are naive with respect to the chosen therapeutic target, is considered to be not very effective, not very reproducible and laborious to implement.

Indeed, although human PBMCs constitute a renewable and readily accessible source of B lymphocytes, this cell population is acknowledged to be the most difficult to immunize (Borrebaeck et al., Proc. Natl. Acad. Sci., 1988, 85, 3995-).

It is accepted that, in order to immunize human PBMCs in vitro, it is absolutely essentially to perform a prior step of depletion of the cells which inhibit the immune response in vitro. The immunosuppressive cells are depleted either by purifying the subpopulations of B, T and dendritic cells (Danielsson et al., Immunology, 1987, 61, 51-55), or by treating the PBMCs with anti-CD56 and/or anti-CD8 antibodies coupled to magnetic beads (application EP 1498426), with lysosomotropic agents (LeuLeuOMe; Borrebaeck et al., Biochem. Biophys. Res. Commun., 1987, 148, 941-946; Borrebaeck et al., Proc. Natl. Acad. Sci., 1988, 85, 3995- and application WO 88/01642) or with sheep red blood cells (rosette method; application EP 0454225). The inhibition of the antibody production observed during the in vitro immunization of PBMCs could involve the cytokine IL-10. This hypothesis originates from three observations. Firstly, during in vitro immunization, the PBMCs treated with the lysosomotropic agent LeuLeuOMe produce antibodies but do not express the IL-10 gene. Secondly, non-treated PBMCs express the IL-10 gene but do not express antibodies (Yamashita et al., Cytotechnology, 2007, 55, 71-77). Thirdly, the incubation of anti-IL-10 antibodies makes it possible to increase antibody production during "in vitro" immunization. The PBMC treatments used to deplete NK cells have, however, the drawback of being toxic and of impairing B lymphocyte functionalities (Mowat et al., Immunology, 1990, 69, 564-569). The immunosuppressive-cell-depleted PBMCs are then incubated in the presence of the antigen and/or of cytokines and/or of cell activators (adjuvants, TLR ligands, CD40 ligand, anti-CD40 antibodies, etc.). The presence of antigen-specific B cells capable of secreting antibodies is then evaluated either by ELISA assay of the culture supernatants, or by ELISPOT measurement of secreting cells. These studies have made it possible to obtain human IgMs specific for various antigens (Borrebeack et al., 1988, mentioned above), thereby indicating that the process of recognition of the Ag by the B lymphocyte is operational and that the concomitant action of cytokines and/or of other cell activators makes it possible to achieve a level of activation sufficient to induce IgM secretion. However, the number of IgM-secreting B lymphocytes obtained after cell fusion or infection with the Epstein-Ban virus often proves to be low (Borrebeack et al., 1988, mentioned above; Chin et al., Immunology, 1994, 81, 428-434; Ishikawa et al., Cytotechnology, 1999, 31, 131-139), thereby suggesting that the in vitro immunization methods which have been used do not result in the induction of strong immune responses. Furthermore, the triggering of an IgG response is even more difficult to obtain than the IgM response, thereby suggesting that isotype switching is not carried out under the experimental conditions used. The low level of IgG response has led to the development of cell culture approaches based on protocols which are even more complex to carry out. One of these approaches consists in using several cell populations having undergone various activation processes. Thus, PBMCs depleted of NK and/or CD8+ cells, from individuals vaccinated against tetanus toxin (TT), are incubated in the presence of a T epitope of TT (pTT) in order to induce T lymphocyte activation. At the same time, PBMCs depleted of NK and/or CD8+ cells and naïve with respect to the Ag are incubated in the presence of an Ag coupled to pTT (pTT-Ag) in order to trigger an IgM-type primary response. The cell populations are then mixed in the presence of fibroblasts transfected with CD32, of an anti-CD40 Ab and of pTT-Ag in order to induce the secondary response which results in the secretion of IgGs specific for the Ag (Duenas et al., Immunology, 1996, 89, 1-7). This approach has been subsequently further optimized by using, on the one hand, PBMCs depleted of NK, CD8+ and IL10+ cells during the primary humoral response induction phase, and on the other hand, the $T_{CD45RO+}$ replacement factor during the secondary response phase. This replacement factor was obtained beforehand from PBMCs depleted of NK and CD8+ cells and then activated with a mitogen. After 3 to 5 days of incubation, the cells are infected with EBV and then fused with a heteromyeloma; this complex technique has made it possible to obtain an antigenic peptide-specific monoclonal IgG4 (Chin et al., BMC Biotechnol, 2007, 7, 51-).

Thus, the in vitro immunization methods used thus far prove to be relatively poorly effective for selecting and inducing antigen-specific human B lymphocytes using the total population of human peripheral blood mononuclear cells. Furthermore, the most complex approaches allow only a small improvement in isotype switching resulting in the obtaining of B cells secreting specific IgGs.

Consequently, the objective of the inventors was to develop an in vitro immunization method using human peripheral blood mononuclear cells which makes it possible to induce the humoral immune response against an antigen more simply.

The transcriptional transactivator (Tat) of the human immunodeficiency virus (HIV) is a protein which has varied activities on the immune system and in particular inhibitory activities in vitro. It has in particular been observed that Tat is capable of inducing lymphocyte apoptosis (Li et al., Science, 1995, 268, 429-31; Westendorp et al., Nature, 1995, 375, 497-500) and of destructing the specific T response which is essential for allowing isotype switching (Viscidi et al., Science, 1989, 246, 1606-8; Subramanyam et al., J. Immunol., 1993, 150, 2544-53). The Tat protein (99 to 103 amino acids depending on HIV strains) comprises 5 domains: (1) the N-terminal domain (positions 1 to 21), which is important for the interaction with cell proteins (2), the cysteine-rich domain (positions 22 to 37) containing 7 cysteine residues (positions 22, 25, 27, 30, 31, 34 and 37) among which 6 are strongly conserved, which is involved in transactivation, (3) the central (core) domain corresponding to positions 38 to 48, also involved in transactivation, (4) the basic domain (positions 49 to 57), which comprises the sequences involved in nuclear localization, transcellular transport and binding to the TAR (Trans-activation response) element of the viral LTR (Long Terminal Repeat), and which is also involved in Tat binding to heparin, and (5) the C-terminal domain (positions 58 to the C-terminal end) which does not possess transactivation activity but contains the glutamine-rich domain (positions 58 to 72) and the RGD motif (arginine-glycine-aspartate; positions 78 to 80), necessary for Tat binding to integrin receptors. In addition, Tat spontaneously forms oligomers when it is dissolved, whereas a Tat derivative containing serines in place of the cysteines remains fully monomeric, thereby indicating that Tat oligomerization is mediated by the cysteines (Kittiworakam et al., J. Biol. Chem., 2006, 281 6, 3105-3115). Furthermore, the same authors have shown that the presence of a single cysteine is sufficient to form Tat oligomers.

The inventors have shown that an Ag coupled to Tat and to an APC ligand is capable of triggering a humoral immune in vitro response using the total PBMC population, i.e. without a prior step of inhibitory cytotoxic cell depletion.

More specifically, the inventors have shown that PBMCs incubated in the presence of the free Tat form cannot trigger an immune response. On the other hand, they produce the secretion of specific IgMs and IgGs when the whole Tat protein or a Tat fragment capable of oligomerizing is coupled to a molecule capable of binding APCs. In addition, when Tat coupled to a molecule capable of binding APCs is used to induce the humoral response, the strength of the specific-Ab response obtained with the total PBMC population is comparable to that obtained with the NK cell-depleted PBMC population. Finally, the inventors have also shown that an Ag other than Tat or than an antigenic fragment of Tat can also trigger the specific-Ab immune response in vitro, in particular the specific-IgG immune response, using the total PBMC population, when it is coupled beforehand to Tat and to a molecule capable of binding APCs.

Consequently, a subject of the present invention is a method for the in vitro immunization of human B lymphocytes, comprising culturing a total population of human peripheral blood mononuclear cells (PBMCs or human PBMCs) in the presence of an antigenic composition comprising at least one antigen covalently bonded both to: (i) a Tat protein or a Tat fragment capable of oligomerizing and (ii) a ligand of a surface molecule specific for antigen-presenting cells.

The method for the in vitro immunization of human B lymphocytes of the invention has the following advantages compared with the prior art methods:
  it makes it possible to efficiently trigger Ag-specific IgG responses, and
  the in vitro immunization is simpler given that it is carried out with a total population of human peripheral blood mononuclear cells, whereas the other methods require the removal of the immunosuppressive cells by means of additional treatments which reduce the efficiency of obtaining immunized B lymphocytes producing Ag-specific antibodies, because they are toxic and modify the B lymphocyte functionality.

Definitions

The term "in vitro immunization of human B lymphocytes" is intended to mean the induction of a humoral response in vitro, i.e. the in vitro production of antigen-specific human antibodies which results from the recognition of said antigen by the immunoglobulins expressed at the surface of naïve human B lymphocytes cultured, in vitro, with the antigen.

The term "naïve B lymphocytes" is intended to mean B lymphocytes which have never encountered the antigen that they could bind via the paratope expressed by their surface immunoglobulin. These B lymphocytes are derived directly from the peripheral blood of a donor who has never been in contact with the antigen. These donors will therefore exhibit a seronegative status with respect to said antigen, i.e. they will exhibit an undetectable titer of serum antibodies specific for said antigen.

The term "antigen" is intended to mean any substance which can be specifically recognized by the immune system and in particular by the antibodies and the cells of the adaptive immune system (B lymphocytes, CD4+ T lymphocytes, CD8+ T lymphocytes).

The term "total population of human peripheral blood mononuclear cells, total PBMC population, PBMCs, total PBMCs, or human PBMCs" is intended to mean all of the mononuclear cells present in human peripheral blood, i.e. the population consisting principally of lymphocytess (B, T, NK) and monocytes, which can be isolated from total human blood by conventional techniques such as density gradient centrifugation.

The term "Tat protein" or "Tat" is intended to mean a protein comprising the amino acid sequence of the Tat protein of an isolate of the human immunodeficiency virus (HIV; natural sequence) or a synthetic sequence derived from one or more natural sequences of Tat and corresponding to a Tat protein having structural and functional characteristics similar to those of an HIV Tat protein.

Figure 6:
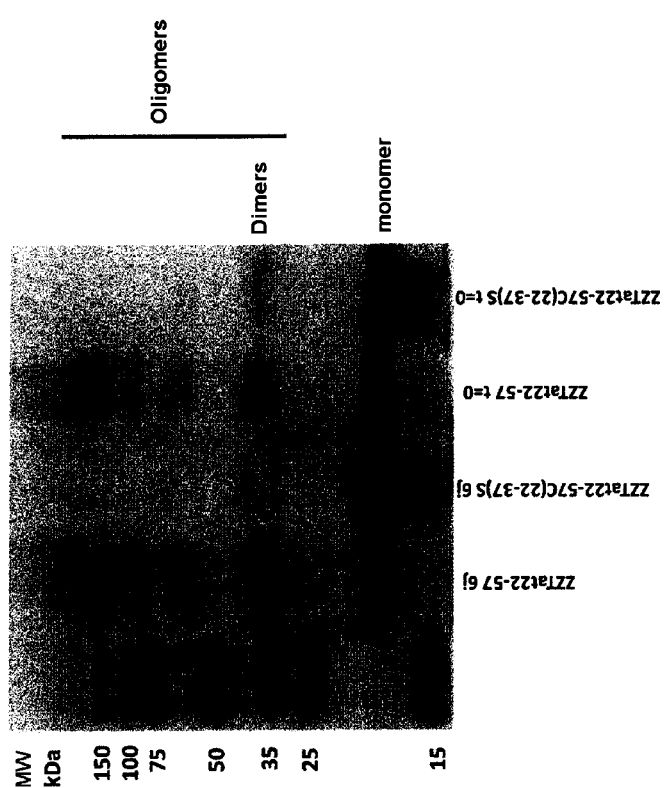

The term "Tat protein or Tat fragment capable of oligomerizing" is intended to mean a Tat protein or a peptide fragment of Tat (Tat peptide) capable of self-associating, i.e. of assembling with one or more identical proteins or fragments so as to form an oligomer molecule consisting of at least two of said proteins or fragments, as illustrated in FIG. 6 for the Tat peptide 22-57.

The term "antigen-presenting cell" or APC, is intended to mean a cell expressing one or more molecules of the class I and class II major histocompatibility complex (MHC) (class I and class II HLA molecules in humans) and capable of presenting antigens to CD4+ T and CD8+ T lymphocytes specific for this antigen. As antigen-presenting cells, mention may in particular be made of dendritic cells (DCs), peripheral blood mononuclear cells (PBMCs), monocytes, macrophages, B lymphocytes, lymphoblastoid lines, and genetically modified human or animal cell lines expressing class I and class II MHC molecules, in particular HLA I and HLA II molecules.

The term "antigen cell surface molecule" is intended to mean a molecule expressed at the surface of antigen-presenting cells.

The term "surface molecule specific for antigen-presenting cells" is intended to mean a surface molecule expressed only on APCs or a molecule expressed essentially on antigen-presenting cells, i.e. a surface molecule expressed on APCs and also on a very limited number of cells other than APCs, and as a result having a high specificity of expression for APCs, i.e. a molecule virtually specific for APCs.

The term "endocytosis receptor" is intended to mean a receptor capable of mediating the endocytosis of a ligand of this receptor.

The term "antibody (Ab)" is intended to mean an immunoglobulin of IgG, IgM, IgA, IgD or IgE class or isotype.

The term "specific antibody" is intended to mean an antibody directed against a particular molecule, commonly referred to as an antigen.

The term "B epitope" is intended to mean the region of an antigen which is recognized by an antibody (B epitope) specific for this antigen. The epitope may in particular be made of a peptide (peptide epitope). It may also be made up of the folding of several zones which are distant in the sequence of a protein. It may also be made up of small structures, known as haptens, which are incapable of triggering the immune response by themselves.

The term "T epitope" is intended to mean the region of an antigen which is recognized by a CD4+ T lymphocyte (CD4+ T epitope) or a CD8+ T lymphocyte (CD8+ T epitope) specific for this antigen. The epitope may in particular be made up of a peptide (peptide epitope).

In accordance with the invention, the in vitro immunization of B lymphocytes is carried out using naïve B lymphocytes, i.e. B lymphocytes derived from an individual or individuals who is or are seronegative with respect to said antigen. The absence of serum antibodies specific for the antigen in the donor(s) is verified by means of a conventional test, in particular an ELISA test.

The PBMC population is obtained from a sample of human peripheral blood, according to conventional techniques for isolating immune system cells, by following the standard protocols known to those skilled in the art.

The total PBMC population is generally isolated by means of the density gradient centrifugation technique, in particular on Ficoll® gradient.

The mononuclear cells isolated from human peripheral blood are then placed in culture under standard conditions (medium, temperature, $CO_2$) for culturing immune system cells, known to those skilled in the art.

The PBMCs are cultured in the presence of an antigenic composition comprising at least the antigen (Ag) covalently bonded both to: (i) a Tat protein or a Tat fragment capable of oligomerizing (Tat), and (ii) a ligand of a surface molecule specific for antigen-presenting cells (Ligand, ligand, APC Ligand, or APC ligand).

The antigenic composition generally comprises three distinct elements, the Ag, Tat or the Tat fragment capable of oligomerizing and the APC Ligand, it being given that the Ag is generally different than Tat or than an antigenic fragment of Tat included in said Tat protein or said Tat fragment capable of oligomerizing. However, when the Ag is Tat or an antigenic fragment of Tat included in said Tat protein or said Tat fragment capable of oligomerzing, then the antigenic composition comprises only two distinct elements, Tat or the Tat fragment capable of oligomerizing, and the APC Ligand.

The covalent bond is in particular generated by covalent chemical coupling (formation of a covalent conjugate) or by the construction of a fusion protein (genetic fusion). The Ag, Tat and the Ligand are bonded either only by covalent chemical couplings or genetic fusions, or by a mixture of the two. In addition, the bonding of the Ag with Tat and the Ligand may be direct or indirect, i.e. the Ag is bonded directly to Tat and to the Ligand (Tat-Ag-Ligand) or Tat and the Ligand are covalently bonded (Tat-Ligand) and the Ag is covalently bonded either to Tat (Ag-Tat-Ligand), or to the ligand (Tat-Ligand-Ag).

The antigen is a natural, recombinant or synthetic antigen, which may correspond to a self molecule or to an attenuated or inactivated pathogenic agent (virus, bacterium, parasite, fungus). The antigen may correspond to a synthetic viral particle, an isolated molecule (protein, polysaccharide, lipid, lipoprotein, glycoprotein or lipopolysaccharide) or a molecule fragment comprising one or more B epitopes, optionally combined with one or more CD4+ T epitopes, in particular in the form of a peptide or of a polypeptide comprising epitopes derived from a single antigen or from several different antigens (polyepitope fragment).

The antigen is preferably a target for the diagnosis or treatment of a disease, preferably chosen from cancers, autoimmune diseases, diseases caused by pathogenic agents (viruses, bacteria, parasites, fungi, etc., agents of infectious diseases or of bioterrorism) or by toxins thereof (botulinum toxin, ricin, anthrax, etc.), chronic inflammatory diseases and graft rejection.

The surface molecule specific for APCs which is targeted by the ligand is a surface molecule expressed essentially on APCs and in particular on B lymphocytes. Preferably, said surface molecule of the APCs is an endocytotis receptor. Among these surface molecules, mention may in particular be made of: (class I and class II) MHC molecules, surface immunoglobulins or membrane immunoglobulins, IgGs interacting with immunoglobulin constant region receptor(s) (FcR and in particular FcγR: FcγRI (CD64), FcγRII (CD32), FcγRIII (CD16)), CD20, integrins (CD11c, MAC1), transferrin receptors, C-type lectin receptors (mannose receptor (CD206), DEC-205 (CD205), DC-SIGN (CD209), LOX1, Dectin-1 (beta-glucan receptor), Dectin-2, Clec9A, Clec12A, DCIR2, FIRE, CIRE), immunoglobulin constant region receptors (FcR and in particular FcγR: FcγRI (CD64), FcγRII (CD32), FcγRIII (CD16)), the TNF receptor (CD40) superfamily and complement receptors.

According to another advantageous embodiment of the invention, the surface molecule specific for APCs which is targeted by the ligand is selected from the group consisting of: membrane immunoglobulins, in particular membrane IgDs and IgMs, immunoglobulin constant region receptors (or FcRs), IgGs interacting with FcR(s), class II MHC molecules, CD20, and C-type lectin receptors.

The ligand is in particular a natural ligand of these APC surface molecules, in particular saccharides which bind C-type lectin receptors, immunoglobulins and fragments thereof comprising the constant region which bind FcRs, proteins and protein fragments which bind the Fc and/or Fab region of immunoglobulins, as described in application FR 2759296, including S. aureus protein A, the BB fragment thereof (BB protein or BB double domain) and the ZZ derivative thereof (ZZ protein or ZZ double domain), the first two proteins binding the Fc and Fab regions of immunoglobulins, whereas the ZZ double domain binds only the Fc region. The BB protein corresponds to the sequence SEQ ID NO: 1 and the ZZ protein to the sequence SEQ ID NO: 2. The ligand is also an envelope protein of a virus (HIV, dengue virus, sindbis virus, etc.) which uses these APC surface molecules as an endocytotis receptor. Alternatively, the ligand is a natural or recombinant antibody directed against these APC surface molecules or a fragment of this antibody containing at least the paratope (antigen-binding domain), such as an Fab, Fab', F(ab')$_2$, Fv or single-chain Fv (scFv) fragment, an Fabc fragment, or an Fab fragment comprising a portion of the Fc domain.

Furthermore, the antigen is optionally covalently or non-covalently combined with other ligands of APC surface molecules, in particular ligands which target different APC surface molecules than the first ligand (L1), in particular surface molecules present on APCs other than that targeted by the first ligand. The noncovalent binding of the other ligands (L2, L3, etc.) is obtained by any means known to those skilled in the art. It may in particular be obtained using a molecule (linker element), in particular a peptide, which has a high and specific affinity for L1, Tat, the Ag or L2. This element is covalently bonded to L1, L2, Tat or the Ag. The affinity of the linker element for its partner, in the complex, is sufficient for it not to immediately dissociate from this complex in vitro. Where L1 or L2 is an antibody, the linker element is in particular a protein or a protein fragment which binds the Fc and/or Fab region of immunoglobulins, as defined above. In addition, where L1 or L2 is a protein or a protein fragment which binds the Fc and/or Fab region of immunoglobulins, as defined above, it acts as linking element for the other ligand which is an antibody.

According to one advantageous arrangement of the above embodiment, the ligand of said surface molecule specific to APCs is selected from the group consisting of or comprising: the BB protein, the ZZ protein, an anti-MHC class II antibody, an anti-IgD, anti-IgG or anti-IgM antibody, an anti-FcgammaR (I, II and/or III), in particular anti-CD32, antibody, an anti-DEC-205, anti-CD209 or anti-CD20 antibody, and a fragment of the above antibodies comprising at least the paratope, in particular an Fab fragment, Fab' fragment, F(ab')$_2$ fragment, Fv fragment, scFv fragment, Fabc fragment or Fab fragment comprising a portion of the Fc region.

The invention encompasses the use of a natural or synthetic Tat protein, in particular a Tat variant obtained by the insertion, the substitution and/or the deletion of one or more Tat amino acids, or of a fragment of said protein or of said variant, which are capable of oligomerizing and of inducing an in vitro immunization, specific for Tat, when they are covalently coupled to an APC Ligand as defined above, in particular to the ZZ protein.

A Tat protein example is the sequence SEQ ID NO: 3 which is that of the NDK isolate of HIV-1 which corresponds to a consensus sequence previously obtained from HIV-1 primary isolate sequences reported in the databases.

The oligomerization of the Tat protein or of the Tat fragment can be carried out with a modified or nonmodified Tat protein or Tat fragment. The oligomerization is preferably carried out using cysteines, but it can also be carried out using any type of amino acid residue and of modification allowing covalent coupling between two peptides or proteins, which are well known to those skilled in the art. By way of nonlimiting example, mention may be made of modified cysteines, in particular penicillamine residues, and also residues respectively functionalized with an azide and an alkyne which couple via click chemistry, and residues functionalized with alkenes which couple via a metathesis reaction.

According to another advantageous embodiment of the invention, said Tat protein or said Tat fragment oligomerizes by means of a cysteine or cysteines. This involves a cysteine or cysteines of the cysteine-rich region or else cysteines which have been added, either in the sequence of said Tat protein or of said Tat fragment, or at one of the ends of said sequence, preferably by means of a cysteine or cysteines of the cysteine-rich region (C22, C25, C27, C30, C31, C34 and/or C37, with reference to the sequence SEQ ID NO: 3).

According to another advantageous embodiment of the invention, said Tat fragment comprises the cysteine-rich (22-37), core (38-48) and basic (49-57) regions.

Tat fragments in accordance with the invention include the Tat peptide 22-57 (said positions being indicated with reference to the sequence SEQ ID NO: 3) and the variants of said peptide which have one to six of the cysteines C22, C25, C27, C30, C31, C34 and C37, the remaining cysteines being replaced by another amino acid, in particular a serine or an alanine.

According to one advantageous arrangement of the previous embodiments, the antigenic composition comprises at least one Ag covalently bonded to (i) a Tat protein or a Tat fragment capable of oligomerizing and (ii) a protein or a protein fragment which binds the Fc and/or Fab region of immunoglobulins, such as the BB protein or the ZZ protein. The Tat fragment is preferably chosen from Tat 22-57 and the variants of said peptide which have one to six of the cysteines C22, C25, C27, C30, C31, C34 and C37, the remaining cysteines being replaced with another amino acid, in particular a serine or an alanine. Preferably, this involves a fusion protein from fusion between the Ag, Tat or the Tat fragment and the ZZ protein or the BB protein. Preferably, said composition also comprises an anti-MHC class II antibody, an anti-FcgammaR (I, II and/or III) antibody, in particular an anti-CD32 antibody, an anti-IgD, anti-IgG or anti-IgM antibody, an anti-DEC-205, anti-CD209 or anti-CD20 antibody, or a fragment of the above antibodies comprising at least the paratope, in particular an Fab fragment, Fab' fragment, F(ab')$_2$ fragment, Fv fragment, scFv fragment, Fabc fragment or Fab fragment comprising an Fc region, noncovalently bound to said protein or said protein fragment which binds the Fc and/or Fab region of immunoglobulins.

According to another advantageous arrangement of the above embodiments, the antigenic composition comprises at least one Ag covalently bonded to (i) a Tat protein or a Tat fragment capable of oligomerizing and (ii) an anti-MHC class II antibody, an anti-FcgammaR (I, II and/or III) antibody, in particular an anti-CD32 antibody, an anti-IgD, anti-IgG or anti-IgM antibody, an anti-DEC-205, anti-CD209 or anti-CD20 antibody, or a fragment of the above antibodies comprising at least the paratope, in particular an Fab fragment, Fab' fragment, F(ab')2 fragment, Fv fragment, scFv fragment, Fabc fragment or Fab fragment comprising a portion of the Fc region. The Tat fragment is preferably chosen from Tat 22-57 and the variants of said peptide which have one to six of the cysteines C22, C25, C27, C30, C31, C34 and C37, the remaining cysteines being replaced with another amino acid, in particular a serine or an alanine.

According to yet another advantageous arrangement of the above embodiments, the antigenic composition comprises at least one Ag covalently bonded to (i) a Tat protein or a Tat fragment capable of oligomerizing and (ii) a protein or a protein fragment which binds the Fc and/or Fab region of antibodies, such as the *Staphylococcus aureus* protein A and the BB fragment thereof, and (iii) an antibody (nonspecific or specific for said antigen), preferably an IgG, or a fragment of said antibody comprising at least the Fc region, and optionally a protein or a protein fragment which binds the Fab region of antibodies, such as *S. aureus* protein A, when the antigen is not already bound thereto. Preferably, the antibody is a whole immunoglobulin and the antigen is covalently bonded to a protein or a protein fragment which binds only the Fab region of antibodies, such as *S. aureus* protein A and the BB fragment thereof. The Tat fragment is preferably chosen from Tat 22-57 and the variants of said peptide which have one to six of the cysteines C22, C25, C27, C30, C31, C34 and C37, the remaining cysteines being replaced with another amino acid, in particular a serine or an alanine.

According to yet another advantageous arrangement of the above embodiments, the antigenic composition comprises at least one Ag covalently bonded to (i) a Tat protein or a Tat fragment capable of oligomerizing and (ii) an antibody specific for said antigen, preferably an IgG, or a fragment of said antibody comprising at least the Fc region, and optionally a protein or a protein fragment which binds the Fab region of antibodies, such as *Staphylococcus aureus* protein A. Preferably, the antibody is a whole immunoglobulin and the complex also comprises a protein or a protein fragment which binds the Fab region of antibodies, such as *Staphylococcus aureus* protein A. The Tat fragment is preferably chosen from Tat 22-57 and the variants of said peptide which have one to six of the cysteines C22, C25, C27, C30, C31, C34 and C37, the remaining cysteines being replaced with another amino acid, in particular a serine or an alanine.

According to another advantageous embodiment of the invention, the antigenic composition comprises at least one B lymphocyte activation factor and/or one B lymphocyte differentiation factor, in particular a factor capable of inducing isotype switching and the production of other immunoglobulin isotypes (IgA, IgG). The factors capable of inducing isotype switching are in particular chosen from one or more of the cytokines IL-1, IL-2, IL-4, IL-5, IL-6, IL-13, IL-21 and TGF-beta. Preferably, said composition comprises IL-21 and optionally IL-4 and/or a CD40 ligand, such as an anti-CD40 antibody or the soluble ligand of CD40, known as CD40L.

The antigenic composition is in soluble or in particulate form. When the composition is in particulate form, the Ag bonded to Tat and to the Ligand(s), and optionally the other constituents, are incorporated inside or at the surface of a particle of the liposome, virosome, nanoparticle, solid microsphere (polymer, silica) or mixed type.

The in vitro immunization method according to the present invention makes it possible to obtain human B lymphocytes immunized with the antigen. These immunized human B lymphocytes produce specific human antibodies of IgG, IgM, IgA and/or IgG isotype, which are secreted into the culture medium.

However, since B lymphocytes have a limited lifetime, it is necessary to immortalize them in order to obtain a continuous production of antibodies specific for the antigen.

Consequently, a subject of the present invention is a method for producing antigen-specific human antibodies, comprising:

a) the in vitro immunization of human B lymphocytes with an antigen (Ag) covalently bonded both to: (i) a Tat protein or a Tat fragment capable of oligomerizing (Tat), and (ii) a ligand of a surface molecule specific for antigen-presenting cells (Ligand or APC Ligand), according to the method for the in vitro immunization of human B lymphocytes of the invention as described above, b) the immortalization of the immunized B lymphocytes obtained in step a), and c) the recovery of the antigen-specific human antibodies produced by the immortalized B lymphocytes obtained in step b).

The antibodies produced according to the in vitro antibody production method of the invention are monoclonal or polyclonal antibodies of IgG, IgM, IgA or IgE isotype, specific for an antigen as defined above.

The immortalization of the B lymphocytes is carried out according to the conventional techniques known to those skilled in the art. It can be carried out by infection with a transforming virus, such as the Epstein-Barr virus (EBV; Lanzavecchia et al., Current Opinion in Biotechnology, 2007, 18, 523-538); preferably, the infection with EBV is carried out in the presence of a TLR agonist such as a CpG motif (Traggiai et al., Nature Medicine, 2004, 10, 871-875). Alternatively, the immortalization is carried out by fusion of the B lymphocytes with a myeloma, in particular a human or murin myeloma, a lymphoblastoid cell line, lymphoma cells or a heteromyeloma line according to conventional cell fusion techniques. Numerous fusion partners for B lymphocytes which make it possible to obtain antigen-specific monoclonal antibody-producing hybridomas have been described. Mention may in particular be made of the human/mouse heteromyeloma lines CB-F7, B6B11, CB-F7, K6H6/B5 and H7NS (vor dem Esche et al., Immunobiology, 2011, 216, 847-853; Kalantarov et al., Human Antibodies, 2002, 11, 85-96; Delvig et al., Human Antibodies Hybridomas, 1995, 6, 42-46); and the MFP-2 trioma line resulting from the fusion of the B6B11 heteromyeloma with a lymph node lymphocyte (Kalantarov et al., Human Antibodies, 2002, 11, 85-96). In addition, the B lymphocytes can be immortalized by combining the infection with EBV and the fusion with a cell partner as defined above.

After the immortalization step, the antigen-specific antibody-producing lymphocytes are identified using conventional techniques known to those skilled in the art, in particular by ELISA, and then they are generally cloned by standard methods such as the limiting dilution technique, so as to obtain B lymphocytes producing an antigen-specific monoclonal antibody. The antigen-specific antibodies produced by the B lymphocytes which are secreted into the culture medium are recovered by simply taking the culture supernatant. The antibodies are then generally purified according to conventional techniques known to those skilled in the art, such as, for example, affinity chromatography.

According to one advantageous embodiment of the invention, said antibody production method comprises an additional step of cloning the immortalized B lymphocytes, between steps b) and c). According to another advantageous embodiment of the invention, said antigen-specific antibodies are human antibodies of IgG isotype.

According to another advantageous embodiment of the invention, they are human monoclonal antibodies, preferably of IgG isotype.

A subject of the present invention is also a kit for carrying out the in vitro immunization method or the antibody production method according to the invention. The kit comprises an antigenic composition as defined above, including in particular the Tat peptide 22-57 or a variant of said peptide which has one to six of the cysteines C22, C25, C27, C30, C31, C34 and C37, the remaining cysteines being replaced with another amino acid, in particular a serine or an alanine.

The antigenic composition according to the invention is prepared by means of the conventional techniques known to those skilled in the art, namely:

the antigen, and the ligands of the APC surface molecules, can be produced by chemical synthesis or by expression of a recombinant DNA in an appropriate eukaryotic or prokaryotic cell system. The peptides and proteins can be synthesized in the solid phase, according to the Fmoc technique, originally described by Merrifield et al. (J. Am. Chem. Soc., 1964, 85, 2149-) and purified by reverse-phase high performance liquid chromatography. The polypeptides and the proteins can be produced from the corresponding cDNAs, cloned into an appropriate eukaryotic or prokaryotic expression vector, the polypeptides or proteins produced in the cells modified by the recombinant vector are purified by any appropriate means, in particular by affinity chromatography. Antibodies directed against APC surface molecules are well known and are commercially available. For example, by way of nonlimiting example, the anti-CD205 (#555831), anti-CD206 (#555952), anti-CD209 (#551186) and anti-HLA-DR (#555556) antibodies are available from Becton-Dickinson. Alternatively, monoclonal antibodies can be produced by the conventional techniques known to those skilled in the art. For example, the monoclonal antibodies are produced from hybridomas obtained by fusion of B lymphocytes from an animal immunized with the APC surface molecule, with myelomas, according to the technique of Köhler and Milstein (Nature, 1975, 256, 495-497); the hybridomas are cultured in vitro, in particular in fermenters, or produced in vivo, in the form of ascites; alternatively, said monoclonal antibodies are produced by genetic engineering as described in American patent U.S. Pat. No. 4,816,567. The humanized antibodies are produced by general methods such as those described in international application WO 98/45332. The antibody fragments are produced from the cloned $V_H$ and $V_L$ regions, from the mRNA of hybridomas or of lymphocytes of immunized mammals; for example, the Fv, scFv or Fab fragments are expressed at the surface of filamentous phages according to the technique of Winter and Milstein (Nature, 1991, 349, 293-299); after several selection steps, the antigen-specific antibody fragments are isolated and expressed in an appropriate expression system, using conventional recombinant DNA cloning and expression techniques. The antibodies or fragments thereof as defined above are purified by the conventional techniques known to those skilled in the art, such as affinity chromatography;

the covalent linking of the antigen (Ag) to Tat or to the Tat fragment (Tat) and to the ligand(s) of APC surface molecules (Ligand(s)) can be carried out by constructing a fusion protein in which the nucleotide sequences encoding the Ag, Tat and the ligand(s) are fused in frame, in the appropriate order, either directly, or by means of a nucleotide sequence encoding an appropriate peptide linker. Depending on the respective sizes of the amino acid sequences of the Ag, Tat and the ligand(s), they are either fused at the level of their ends (N-terminal end of one of the sequences fused to the C-terminal end of the other sequence) or one of the sequences inserted into the other sequence at an appropriate site which has no harmful effect on the immunogenicity of the antigen and the binding of the ligand(s) to its (their) receptor expressed at the surface of the APCs. Alternatively, the Ag, Tat and the ligand(s) can be covalently coupled, by any appropriate means. The coupling is carried out by means of reactional groups initially present on or previously introduced onto the antigen, Tat and the ligand(s). The coupling can in particular be carried out at the level of amino acids of which the side chain comprises a reactive function. Among these amino acids, mention may be made of polar amino acids comprising a function: —OH [serine (S), threonine (T) or tyrosine (Y)], —SH [cysteine (C)], —NH$_2$ [lysine (K) or arginine (R)], —COOH [aspartic acid (D) or glutamic acid (E)], and polar amino acids with a side chain functionalized by addition of a reactive function. The antigen is coupled to Tat and/or to the ligand(s) by any appropriate means; these means which are known to those skilled in the art include, in particular, coupling using homobifunctional reagents such as glutaraldehyde or dithiobis(succinimidyl propionate). Preferably, the coupling is carried out using heterobifunctional reagents, in particular m-maleimidobenzoyl-N-hydroxysuccinimide (SMCC) or sulfo-SMCC, which each contain a maleimide group capable of reacting with free thiols. In this case, the SMCC is covalently bonded beforehand to an amine function present on the Ag, Tat or the ligand(s). At the same time, another heterobifunctional reagent (such as N-succinimidyl S-acetylthioacetate, which contains a thioester group that is cleavable with hydroxylamine or succinimidyl pyridyl dithiopropionate, which contains a disulfide bridge that can be reduced under mild conditions), is linked to an amine function of the second partner, which is the Ag, Tat or one of the ligands. The second partner is then treated with hydroxylamine or with a reducing agent in order to allow release of the thiol. The thiolated compound is then incubated with the compound having incorporated the maleimide and the coupling is obtained by reaction of the thiol group with the maleimide group. This type of covalent coupling is in particular described in Leonetti et al., J. Exp. Med., 1999, 189, 1217-1228. It is also possible to release a thiol group already present on one of the compounds in order to subsequently carry out the coupling thereof to another compound which has been modified beforehand using SMCC. This method, which is often used to couple antibodies to ligands, is in particular described in Ishikawa et al, J Immunoassay, 1983, 4, 209-327;

the noncovalent complexes are prepared by bringing the second ligand (L2) into contact with the antigen covalently bonded to the first ligand and to Tat (L1-Ag-Tat, the order of L1 and of the Ag being of no importance when it is a fusion protein), under conditions which allow the two partners to interact. This interaction can involve a linker element, in particular a protein or a peptide, which has a high and specific affinity for one of the partners of the complex (Ag, Tat or L1). In particular, the affinity of the linker element for this partner, in the complex, is sufficient for it not to immediately dissociate from this complex in vitro. When one of the ligands is an immunoglobulin, the linker element is an element for binding to immunoglobulins as described in application FR 2759296. When one of the ligands is an immunoglobulin or an immunoglobulin fragment and the other a protein or a protein fragment which binds immunoglobulins, L1 and L2 may link together directly.

The implementation of the invention uses, unless otherwise indicated, conventional immunology, cell culture, cell biology, molecular biology and recombinant DNA methods which are known to those skilled in the art.

Figure 2:
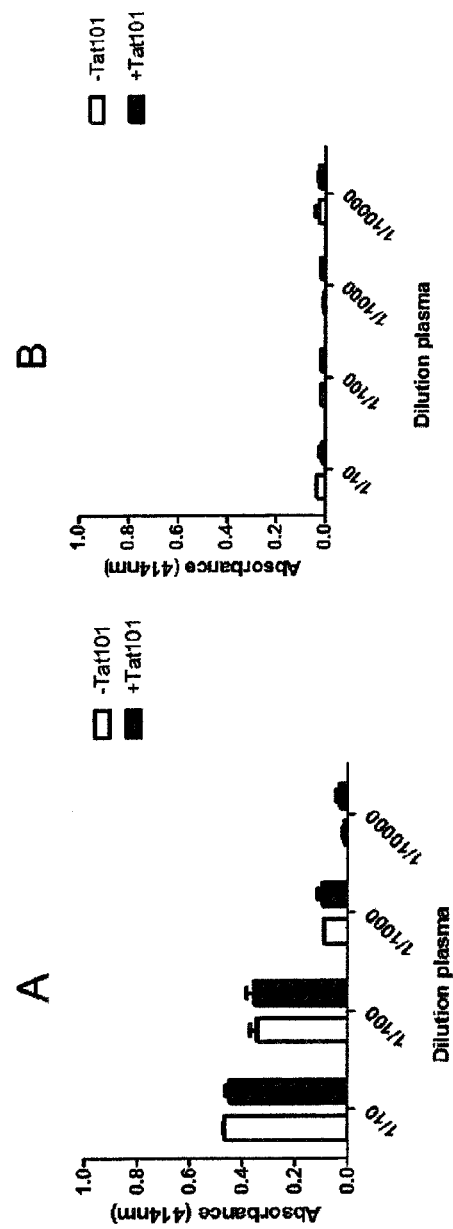
Figure 3:
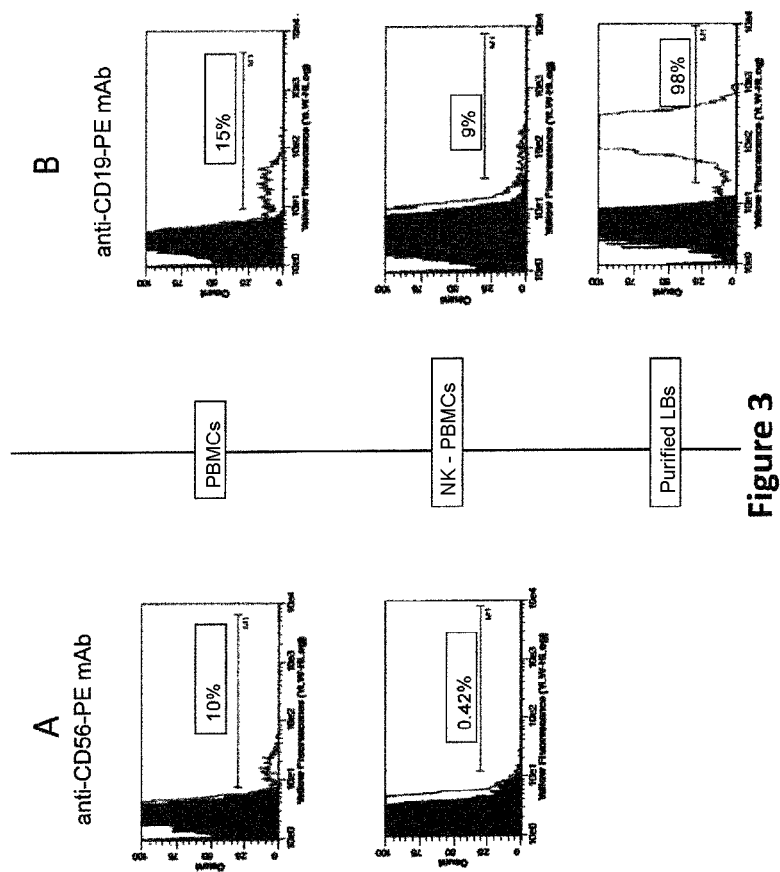
Figure 4:
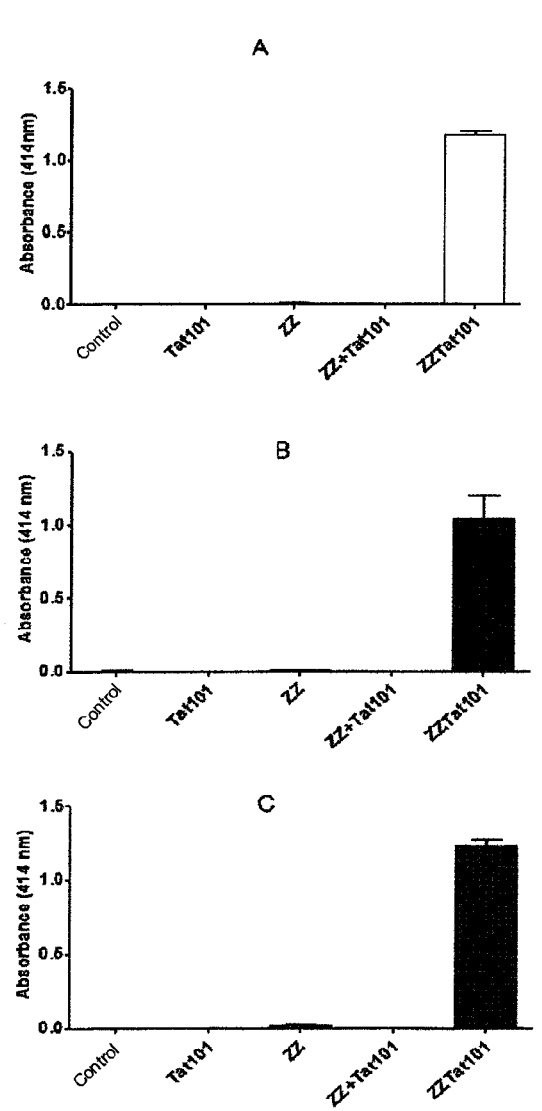
Figure 5:
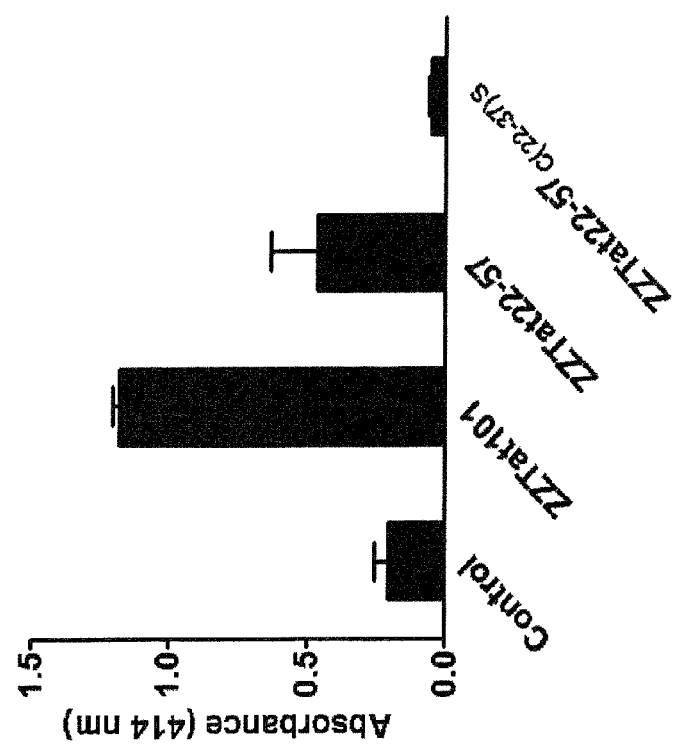
Figure 7:
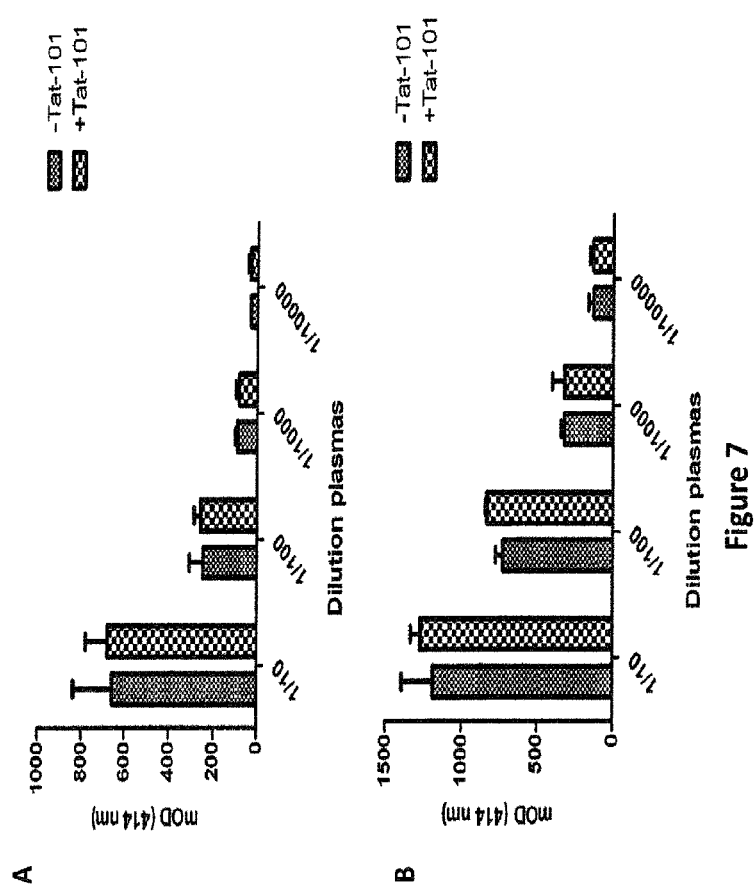
Figure 8:
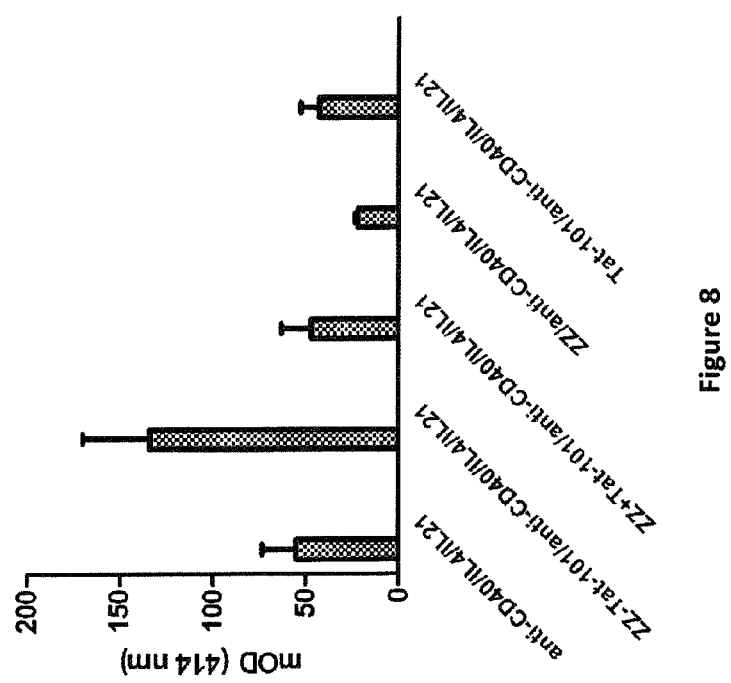
Figure 9:
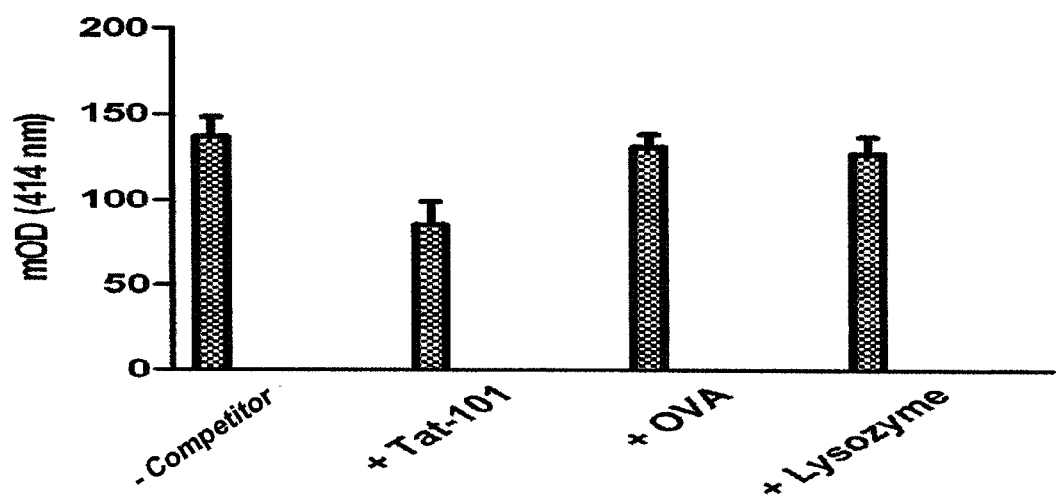
Figure 10:
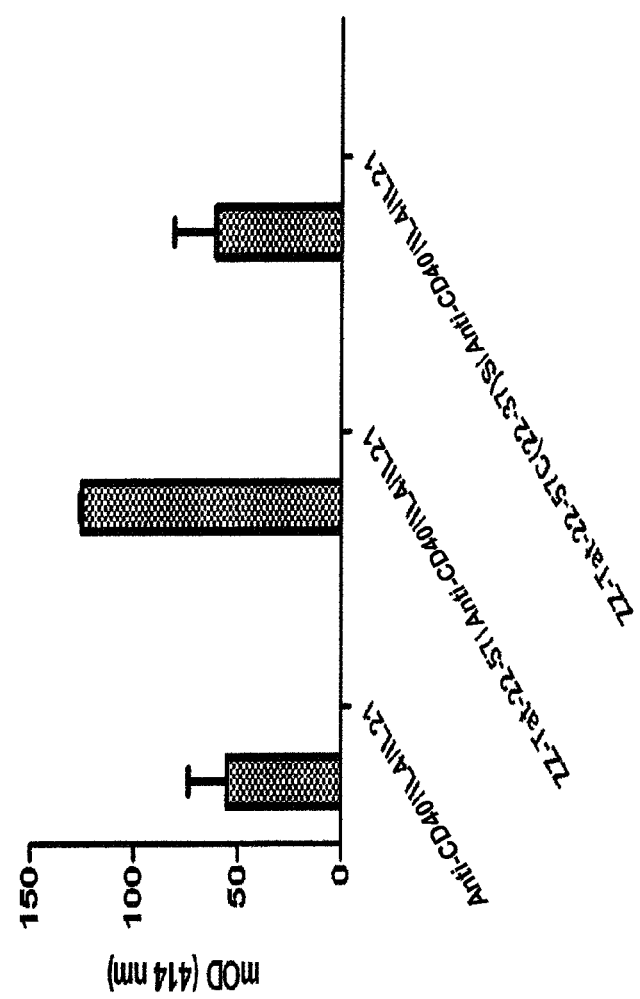
Figure 11:
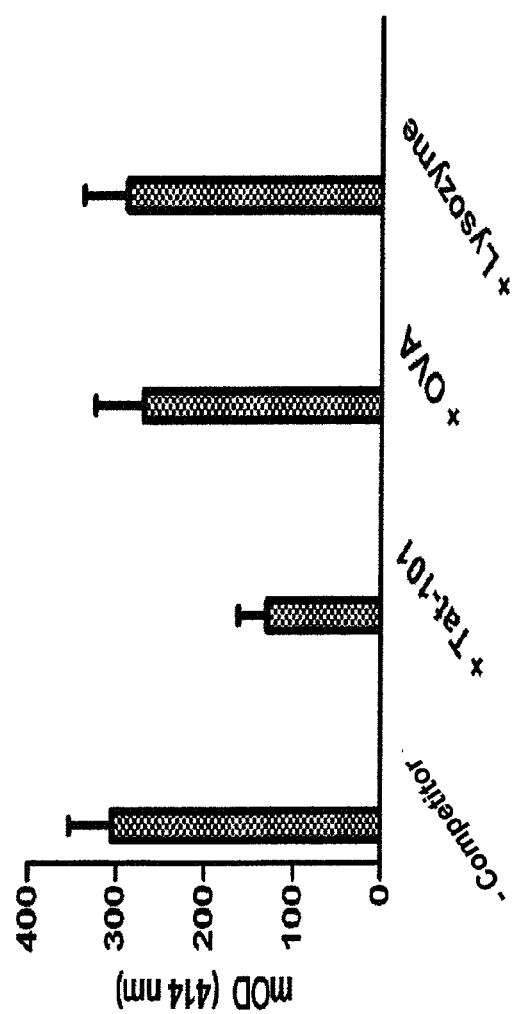
Figure 12:
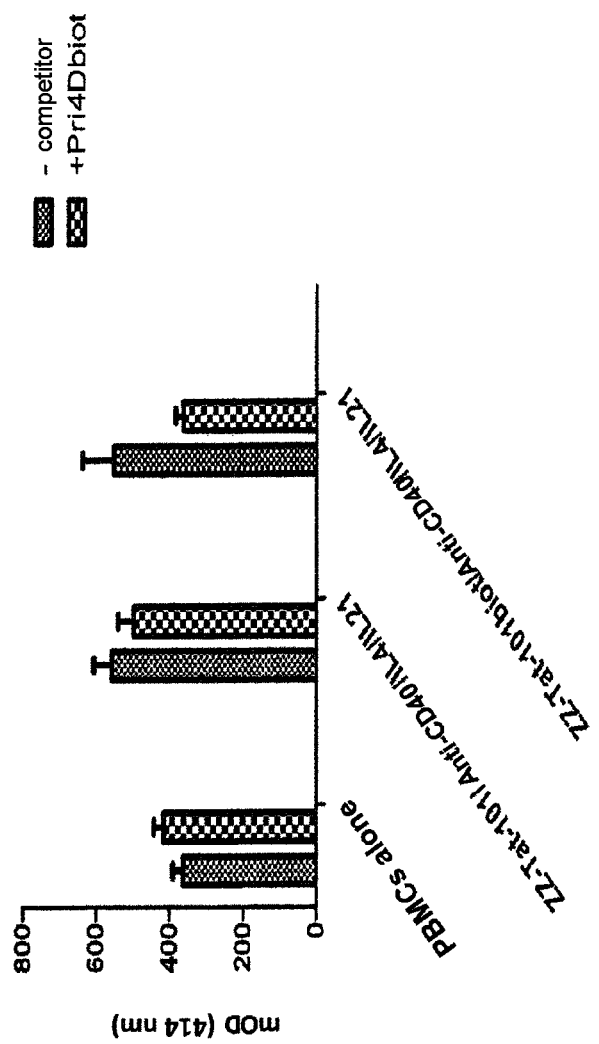
Figure 13:
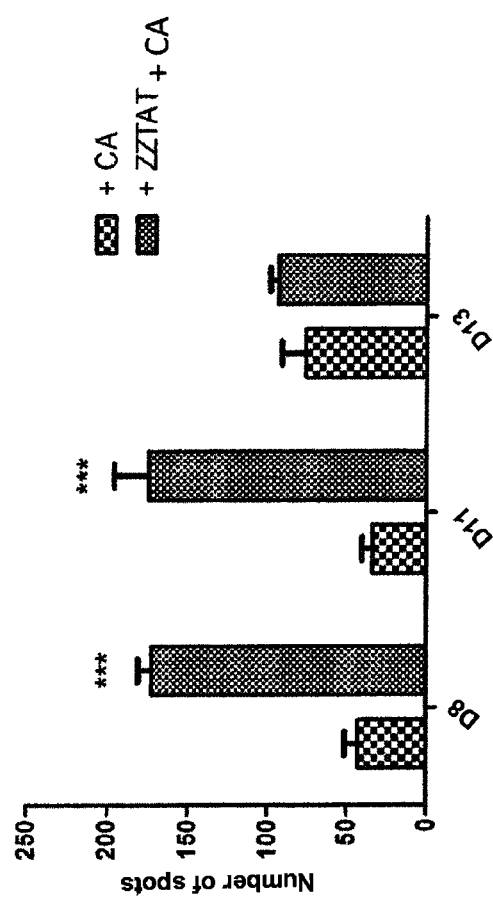
Figure 14:
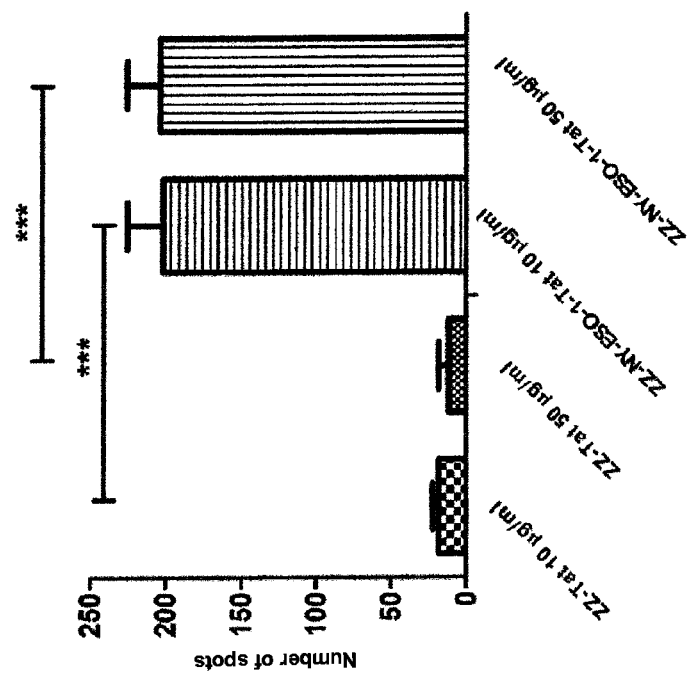

In addition to the preceding arrangements, the invention also comprises other arrangements that will emerge from the description which follows, which refers to exemplary embodiments of the method which is the subject of the present invention and also to the appended drawings, in which:

FIG. 1 shows that the transactivation activity of the Tat101 protein is modified when it is fused to the ZZ double domain. A HeLa line stably transfected with a plasmid encoding the HIV-1 LTR sequence and encoding the sequence of the EGFP protein was incubated with the free Tat101 protein or the Tat101 fused to ZZ (ZZ-Tat101) for 45 hours at 37° C. The EGFP expression was then examined by flow cytometry (FACS);

FIG. 2 illustrates the measurement of the anti-Tat101 specific antibodies before the in vitro immunization of human PBMCs. A. The anti-Tat101 IgM response in the individual plasmas of healthy donors (EFS [French Blood Bank] Rungis, France). The anti-Tat101 IgM response was evaluated using an immunoenzymatic assay. Series of plasma dilutions were incubated overnight in plates adsorbed with Tat101, in the presence or absence of Tat101 as competitor (final concentration of 2 μg/ml). B. The anti-Tat101 IgG response in the individual plasmas of healthy donors (EFS [French Blood Bank] Rungis, France). The anti-Tat101 IgG response was evaluated using an immunoenzymatic assay. Series of plasma dilutions were incubated overnight in plates adsorbed with Tat101, in the presence or absence of Tat101 as competitor (final concentration of 2 µg/ml). After three washing cycles, 200 µl of Ellman's reagent were added and the absorbance at 414 nm was measured after 1 h;

FIG. 3 shows the purity of the cell population revealed by flow cytometry. A. The PBMCs and the NK-cell-depleted PBMC fraction were incubated with (gray histogram) or without (black histogram) a phycoerythrin-labeled anti-human CD56 antibody. B. The PBMCs, the NK-cell-depleted PBMC fraction and the purified B lymphocytes were incubated with (gray histogram) or without (black histogram) a phycoerythrin-labeled anti-human CD19 antibody;

FIG. 4 shows the effect of ZZTat101 on the IgM antibody response. Anti-Tat101 antibody response of PBMC-NK ($1\times10^6$ cells/well) (A), PBMC ($1\times10^6$ cells/well) (B), and of purified B lymphocytes (C) after immunization with the ZZTat101 fusion protein (final concentration 10 µg/ml) or its constituents: ZZ, Tat101, or a mixture of ZZ and of Tat101 (final concentration 10 µg/ml). After a restimulation, on days three and seven, of the immunization, the presence of specific anti-Tat101 IgMs in the pure culture supernatant was determined using an immunoenzymatic assay in the presence or absence of Tat101 as competitor (2 µg/ml). After three washing cycles, 200 µl of Ellman's reagent were added and the absorbance at 414 nm was measured after 2 h. The specific signal corresponds to the signal in the presence of Tat101 subtracted from the signal in the absence of Tat101;

FIG. 5 shows that the 22-57 region of Tat101 is sufficient to initiate an IgM immune response, and that the response depends on the presence of the seven cysteines of Tat. NK-depleted PBMCs were incubated with the ZZTat101 fusion protein or its derivatives, ZZTat22-57 including the cysteine-rich (23-37), core (38-48) and basic (49-57) regions, and ZZ-Tat22-57$_{C(22-37)S}$ corresponding to ZZTat22-57 with the seven cysteines replaced with serines. The antigens were added a second time, at the same concentration, after three days of incubation. The culture supernatants were taken on the seventh day and were used pure in order to determine the presence of specific anti-Tat101 IgMs using an immunoenzymatic assay. In this assay, the supernatants were incubated in plates in the presence or absence of a solution of Tat101 (2 µg/ml) which was used as a competitor for the binding to the plates. After three washing cycles, 200 µl of Ellman's reagent were added and the absorbance at 414 nm was measured after 2 h. The specific signal corresponds to the signal in the presence of Tat101 subtracted from the signal in the absence of Tat101;

FIG. 6 represents the SDS-PAGE analysis of the capacity of ZZ-Tat22-57 and ZZ-Tat22-57$_{C(22-37)S}$ to form oligomers. In this experiment, ZZTat22-57 is dissolved in a PBS buffer (10 µg of protein in 10 µl of buffer) in the presence of an excess of maleimide in order to block the free cysteines present as soon as dissolution takes place. Another solution of ZZTat22-57 is incubated for 6 days at roomtemperature in PBS. After 6 days, the residual free cysteines are blocked with an excess of maleimide. The two samples of ZZTat22-57 (d=0 and d=6) and also the ZZTat22-57C(22-37)S protein devoid of cysteine are then deposited on an SDS-PAGE gel in the absence of reducing agent in order to evaluate the presence of monomeric and oligomeric forms;

FIG. 7 shows the analysis of the presence of anti-Tat IgM or IgG Abs in the plasmas from leucocytes/platelet concentrate residues. In order to evaluate the presence of anti-Tat antibodies, plasma dilutions were incubated in the presence or absence of a solution of Tat101 in microtitration plates, the wells of which were preadsorbed with the Tat protein. The presence of IgM was evaluated using a peroxidase-coupled anti-IgM Ab (A), while the presence of IgG was evaluated using a peroxidase-coupled anti-IgG Ab (B);

FIG. 8 shows that only the supernatants resulting from the incubation with ZZ-Tat101 contain IgGs capable of binding the plates adsorbed with Tat101. The PBMCs were incubated with an activation mixture (anti-CD40 at 1 µg/ml, IL-4 at 10 ng/ml, IL-21 at 50 ng/ml) and in the absence or presence of various Ags used at 10 µg/ml (ZZ-Tat101, ZZ, ZZ+Tat101, Tat101). The supernatants were then sampled at various times and the presence of antibodies was evaluated by immunoenzymatic assay using a peroxidase-coupled goat anti-human IgG antibody;

FIG. 9 shows that the Abs contained in the supernatants resulting from the incubation with ZZ-Tat101 which bind the plate adsorbed with Tat101 are indeed specific for Tat. In order to determine the specificity of binding to the plates, the supernatants incubated in the absence of Ag or with ZZ-Tat101 were incubated on the microtitration plates in the presence of solutions containing either the Tat101 protein or two unrelated Ags (ovalbumin, referred to as OVA, and lysozyme). The Ab binding to the plates was determined by immunoenzymatic assay using a peroxidase-coupled goat anti-human IgG antibody;

FIG. 10 shows that the 22-57 region of Tat is sufficient to cause IgG secretion and that the presence of the cysteines located in the 22-37 region is essential for obtaining the effect in vitro. The PBMCs were incubated with an activation mixture (anti-CD40 at 1 µg/ml, IL-4 at 10 ng/ml, IL-21 at 50 ng/ml) and in the absence or presence of ZZ-Tat22-57 or of ZZ-Tat22-57$_{C(22-37)S}$. The supernatants were then sampled at various times and the presence of antibodies was evaluated by immunoenzymatic assay using a peroxidase-coupled goat anti-human IgG antibody;

FIG. 11 shows that the Abs contained in the supernatants resulting from the incubation with ZZ-Tat22-57 which bind the plate adsorbed with Tat101 are indeed specific for Tat. In order to determine the specificity of binding to the plates, the supernatants incubated in the absence of Ag or with ZZ-Tat22-57 were incubated on the microtitration plates in the presence of solutions containing either the Tat101 protein, or two unrelated Ags (ovalbumin, referred to as OVA, and lysozyme). The Abs binding to the plates was determined by immunoenzymatic assay using a peroxidase-coupled goat anti-human IgG antibody;

FIG. 12 shows that biotin becomes capable of triggering, "in vitro", an IgG response when it is coupled beforehand to ZZ-Tat101. The PBMCs were incubated in the presence or absence of an activation mixture (anti-CD40 at 1 µg/ml, IL-4 at 10 ng/ml, IL-21 at 50 ng/ml) and in the absence or presence of ZZ-Tat101biot. The supernatants were sampled 11 days later. Microtitration plates were adsorbed with a biotinylated peptide, known as Pri4Dbiot, the peptide sequence of which is not related to that of ZZ-Tat101. The supernatants were then incubated on the plates in the presence or absence of a solution containing an excess of Pri4Dbiot peptide. The presence of antibodies was finally evaluated by immunoenzymatic assay using a peroxidase-coupled goat anti-human IgG antibody;

FIG. 13 shows that, after in vitro immunization, the PBMCs contain cells secreting anti-Tat IgG. The PBMCs were incubated in the presence of an activation mixture (anti-CD40 at 1 µg/ml, IL-4 at 10 ng/ml, IL-21 at 50 ng/ml) and in the absence or presence of ZZ-Tat101. Eight, eleven or thirteen days later, the cells were transferred onto ELISPOT plates preadsorbed with Tat101. After one day of incubation at 37° C., the plates were washed in order to remove the cells and a peroxidase-coupled anti-IgG antibody was added. After 1 h of incubation at 20° C., the plates are washed and a mixture of BCIP/NBT is added in order to reveal the enzymatic activity in the wells. The spots are visualized and counted using an ELISpot reader;

FIG. 14 shows that, after in vitro immunization, the PBMCs contain cells secreting anti-NYESO-1 IgG. The PBMCs were incubated in the presence or absence of an activation mixture (anti-CD40 at 1 µg/ml, IL-4 at 10 ng/ml, IL-21 at 50 ng/ml) and in the absence or presence of ZZ-NY-ESO-1-Tat or of ZZ-Tat. Eleven days later, the cells were transferred onto ELISpot plates preadsorbed with the NY-ESO-1 peptide. After one day of incubation at 37° C., the plates were washed in order to remove the cells and a peroxidase-coupled anti-IgG antibody was added. After 1 h of incubation at 20° C., the plates were washed and a mixture of BCIP/NBT was added in order to reveal the enzymatic activity in the wells. The spots were visualized and counted using an ELISpot reader. The figure shows the number of spots after deduction of those counted when the PBMCs are incubated only with the cocktail of activators.

EXAMPLE 1: STUDY OF THE TRANSACTIVATING POWER OF TAT101 AND ZZ-TAT101

1. Materials and Methods
1.1 Synthesis of the Tat Protein

The Tat protein, called Tat or Tat101 (SEQ ID NO: 3) has the sequence of the NDK isolate of HIV-1 (Groenink et al., J Virol., 1991, 65, 1968-1975) which corresponds to a consensus sequence previously obtained from 66 sequences of HIV-1 primary isolates reported in the SWISSPROT and TrEMBL databases between 1999 and 2000 (Kittiworakarn et al., J.Biol.Chem., 2006, 281 3105-3115). The chemical synthesis of Tat was carried out by means of the Fmoc/tert-butyl strategy using an Applied Biosystems 433A automatic peptide synthesizer. The chemical process uses 0.1 mmol of Fmoc-Asp(OtBu)-PAL-PEG-PS resin, a 10-fold excess of each amino acid, dicyclohexylcarbodiimide/1-hydroxy-7-azabenzotriazole and diisopropylethylamine/N-methylpyrrolidone. Glutamine 54 was optionally incorporated manually. The cleavage and the deprotection were carried out using a trifluoroacetic acid/triisopropylsilane/water mixture (9.5/0.25/0.25, v/v/v). The crude material was precipitated twice with tert-butyl methyl ether, cooled to 4° C., then dissolved in an aqueous 15% acetic acid solution. The crude protein was then purified by reverse-phase high performance liquid chromatography (HPLC), on a VYDAC® C18 column (Hesperia) or a Jupiter™ C4 column. The S(tBu) groups were removed from the cysteines using a degassed 0.1 M phosphate buffer, pH 8.5, containing 6 M of urea (6 M) and dithiothreitol (50 eq/Cys). After having finished the deprotection of the cysteines, the mixture was acidified to pH 2.2 and purified by HPLC on a C4 column. The completely reduced Tat proteins were stored in lyophilized form at −20° C. The protein synthesized was characterized by mass spectrometry and by amino acid analysis.

1.2 Construction, Expression and Purification of the ZZ-Tat101 and ZZ-Tat22-57 Proteins The ZZTat101 fusion protein was constructed using a synthetic nucleotide sequence SEQ ID NO: 4 encoding Tat101, flanked by KpnI and BamHI sites, respectively in 5' and in 3'. The nucleotide sequence was inserted between the KpnI and BamHI sites of the pCP vector (Drevet et al., Protein Expression Purif 1997, 10, 293-300) encoding the ZZ protein having the amino acid sequence SEQ ID NO: 2, a double domain for binding to the IgG Fc region derived from the B domain of *Staphylococcus aureus* protein A, previously described (Nilsson et al., Protein Engineering 1987, 1, 107-113).

The ZZTat22-57 fusion protein was constructed similarly using a synthetic nucleotide sequence SEQ ID NO: 5 encoding the peptide 22-57 of Tat101, flanked by KpnI and BamHI sites, respectively in 5' and in 3'.

The ZZTat22-57$_{C(22-37)S}$ fusion protein contains Tat22-57$_{C(22-37)S}$, a Tat22-57 variant in which all the cysteines of the cysteine-rich region (C22, 25, 27, 30, 31, 34 and 37) have been replaced with serines, fused to ZZ. The ZZTat22-57$_{C(22-37)S}$ fusion protein was constructed similarly, using a synthetic nucleotide sequence SEQ ID NO: 6 encoding Tat22-57$_{C(22-37)S}$, flanked by KpnI and BamHI sites, respectively in 5' and in 3'.

Bacteria (*E. coli* BL21(DE3)pLysS) were then transformed with the different plasmids. The fusion proteins were expressed and then purified on an affinity column (IgG SEPHAROSE™6 Fast flow, Amersham). The purity was evaluated by gel electrophoresis. The proteins were produced with yields ranging between 1 and 5 mg/l of culture. The products were stored in lyophilized form until use.

1.3 Evaluation of the Transactivation Activity of Tat101 and ZZ-Tat101

The transactivation activity was evaluated using the protocol described by Kittiworakam et al. (J. Biol. Chem., 2006, 281, 3105-15).

2. Results

The capacity of Tat to trigger the immune response was studied using a Tat protein of 101 residues, called Tat101, which originates from a previously described viral isolate (Groenink et al., J Virol., 1991, 65, 1968-1975). Since the transactivation activity of Tat can cause the dysregulation of numerous genes (Li et al., AIDS, 2010, 1609-23; Darbinian-Sarkissian et al., J. Cell Physiol., 2006, 208, 506-15) and have activating or inhibiting effects, the transactivating power of Tat101 and ZZTat101 was evaluated. The protocol used is based on the incubation of the proteins in the presence of HeLa cells transfected with a plasmid encoding the HIV-1 LTR sequence and the GFP sequence (Kittiworakam et al., J. Biol. Chem., 2006, 281, 3105-15). As can be seen in FIG. 1, the wild-type Tat101 protein efficiently transactivates since it increases the expression of GFP by the HeLa line. On the other hand, the ZZTat101 does not cause any increase in the expression of GFP, thereby indicating that the fusion protein is devoid of the transactivation activity of Tat and that it cannot therefore dysregulate genes by means of this activity.

EXAMPLE 2: THE IN VITRO INCUBATION OF PBMCS IN THE PRESENCE OF ZZ-TAT101 OR OF ZZ-TAT22-57 CAUSES THE SECRETION OF TAT-SPECIFIC IGMS

1. Materials and Methods
1.1 Human Peripheral Blood Mononuclear Cell Purification The blood (approximately 250 ml) of healthy donors (negative for HIV1/2, HTLV-I/II, HCV and HBsAg) comes from the Etablissement Français du Sang [French Blood Bank] (France). The PBMCs are isolated by two successive density gradient centrifugations (HISTOPAQUE®-1077, Sigma) at 1200 g for 30 min. The donor plasmas are isolated and stored at −80° C. for the serological analysis. The cells are rinsed in PBS (10 mM potassium phosphate, pH 7.4, and 150 mM NaCl) to which 2 mM EDTA has been added.

1.2 Cell Separation
B Lymphocyte Isolation

The B lymphocytes are isolated from the PBMCs using MACS® microbeads according to the protocol of the manufacturer (Miltenyi Biotec). Briefly, $5\times10^8$ PBMCs are washed in MACS buffer (PBS to which 2 mM EDTA and 0.5% BSA have been added), at 4° C. Anti-CD20 microbeads (150 µl) are added (5 µl of anti-CD20 microbeads for $10^7$ cells) and the cells are incubated at 4° C. for 15 min. The cells are rinsed, centrifuged, and passed through magnetic columns. The enrichment is evaluated by flow cytometry analysis (GUAVA®, Millipore), using a phycoerythrin-conjugated anti-human CD19 antibody (Miltenyi Biotec).

NK (Natural Killer) Cell Depletion

The NK cells are depleted from PBMCs using MACS® microbeads according to the protocol of the manufacturer (Miltenyi Biotec). Briefly, $1\times10^8$ PBMCs are washed in MACS buffer (PBS to which 2 mM EDTA and 0.5% BSA have been added), at 4° C. Anti-CD56 microbeads (800 µl) are added (80 µl of anti-CD56 microbeads for $10^7$ cells) and the cells are incubated at 4° C. for 15 min. The cells are rinsed, centrifuged, and passed through magnetic columns. The enrichment is evaluated by flow cytometry analysis (GUAVA®, Millipore) using a phycoerythrin-conjugated anti-human CD56 antibody (Miltenyi Biotec).

The PBMCs, the purified B lymphocytes and the NK-depleted PBMCs are cultured at a density of $1\times10^6$ cells/ml in RPMI-1640 medium supplemented with L-glutamine (2 mM), penicillin (50 IU/ml), streptomycin (50 µg/ml), 50 µM beta-mercaptoethanol and 10% of heat-inactivated fetal calf serum.

1.3 Flow Cytometry Analysis

The flow cytometry was used to analyze various cell membrane markers and to thus evaluate the quality of the cell separation. All the flow cytometry labeling procedures were carried out at 4° C. in PBS to which 1% of BSA had been added. $10^5$ cells of each cell subpopulation (PBMCs, purified B lymphocytes and NK-depleted PBMCs) are labeled for 35 min with a phycoerythrin-conjugated anti-human CD19 antibody (Miltenyi Biotec) and with a fluorescein-conjugated anti-human CD56 antibody (BD Biosciences), and then washed. The cells are then fixed with 4% paraformaldehyde for 10 min at room temperature and washed before the FACS analysis, using a three-color flow cytometer (GUAVA®).

1.4 Preparation of the Plates for Immunoenzymatic Assay (ELISA)

96-well plates (MAXISORP™, Nunc) were coated with Tat peptides (P1(1-15), P10(46-60), P15(66-80), P16(71-85), P18(86-101)), Tat101 and BSA (0.1 µg/well in 50 mM sodium phosphate buffer, pH 7.4), overnight at room temperature. The plates were washed once with washing buffer (0.01 M potassium phosphate buffer, pH 7.4, containing 0.05% of Tween 20) and saturated with buffer for immunoenzymatic assay (EIA) (0.1 M phosphate, pH 7.4, containing 0.15 M NaCl, 0.1% BSA and 0.01% sodium azide) and stored at 4° C. Before use, the plates were washed three times with washing buffer.

1.5 Preparation of the Conjugated Antibody

The monoclonal antibodies (mAbs) are bonded to acetylcholinesterase (AChE) using a previously described protocol (Grassi et al., J. Immunol. Methods, 1989, 123, 193-210). Briefly, F(ab')2 fragments are obtained from purified antibodies by treatment with pepsin in an acetic medium. Fab' fragments are obtained from the F(ab')2 fragments by reduction in the presence of 0.02 M 2-mercaptoethylamine, and then coupled to AChE using the heterobifunctional reagent N-succinimidyl-4-(N-maleimidomethyl)cyclohexane-1-carboxylate (SMCC), as previously described (Grassi et al., J. Immunol. Methods, 1989, 123, 193-210).

1.6 Measurement of Acetylcholinesterase Activity

The AChE activity was measured using the Ellman method (Ellman et al., Biochem. Pharmacol., 1961, 7, 88-95). Ellman medium comprises a mixture of $7.5\times10^{-4}$ M acetylthiocholine (enzymatic substrate) and $2.5\times10^{-4}$ M 5,5'-dithiobis(2-nitrobenzoic acid) (DTNB: reagent for colorimetric measurement of thiols), in a 0.1 M phosphate buffer, pH 7.4. The enzymatic activity is expressed in Ellman units (EU). One EU is defined as the amount of enzyme which produces an increase in adsorbance of one unit for 1 min in 1 ml of medium, for an optical path length of 1 cm, and corresponds to approximately 8 ng of enzyme.

1.7 Detection of Anti-Tat Antibodies

The presence of anti-Tat antibodies was analyzed in the plasmas from blood donors and in the in vitro immunization cell culture supernatants. 50 µl of series of dilutions of plasma or of in vitro immunization well supernatants were transferred into microplates coated with Tat, with Tat peptides and with BSA, with 50 µl of EIA buffer or 50 µl of Tat101 (2 µg/ml in EIA buffer) in order to determine the specificity. After an overnight period at 4° C., the plates were washed three times with washing buffer before revealing the presence of anti-Tat antibodies. To detect the anti-Tat IgMs, 50 µl of rabbit anti-human IgM antibody (1 µg/ml, Jackson Immunoresearch) were added to the plates, which were incubated overnight at 4° C. After washing, 50 µl of 2.5 EU/ml of AChE-coupled mouse-anti-rabbit immunoglobulin antibody were added for 4 h at roomtemperature. To detect the anti-Tat IgGs, 50 µl of AChE-coupled mouse anti-human IgG antibody (monoclonal antibody from Meridan Life Science; 2.5 EU/ml) were added and incubated overnight at 4° C. After three washing cycles, 200 µl of Ellman's reagent were added and the adsorbance was measured at 414 nm, after 1 h.

1.8 In Vitro Immunization

The in vitro immunization of the PBMCs, NK-depleted PBMCs and purified B lymphocytes was carried out in 24-well plates, at $1\times10^6$ cells per well in a final volume of 1 ml of medium (RPMI-1640 supplemented with L-glutamine (2 mM), penicillin (50 IU/ml), streptomycin (50 µg/ml), 50 µM beta-mercaptoethanol and 10% of heat-inactivated fetal calf serum). The various cell populations were incubated in vitro, in the presence or absence of, respectively, ZZTat101, ZZ, Tat101, and a mixture containing ZZ+Tat101. The culture wells were incubated with 50 µl of a solution of 200 ng/ml of each antigen. On D7, the well supernatants were tested by ELISA in order to detect the specific antibodies produced by the cells. In a second series of experiments, the cells were incubated in vitro with 10 ng/well of various ZZTat101-related fusion proteins, i.e., ZZTat22-57$_{C(22-37)S}$ and ZZTat22-57. The experiments were then carried out like the previous ones.

2. Results 2.1 Selection of Blood Samples Free of Anti-Tat Antibodies

Since the objective of the present study is to evaluate the capacity of Tat101 to induce an in vitro immune response with B lymphocytes which are naïve with respect to this antigen, blood samples were selected beforehand, using as criterion the absence of anti-Tat101 antibodies in their plasmas. In order to evaluate the presence of anti-Tat101 antibodies, series of dilutions of various plasma samples were incubated on microplates adsorbed with Tat101, or with BSA, in the presence or absence of a solution containing an excess of Tat101. The interaction between the antibodies and the protein adsorbed on the microplate was revealed using AChE-labeled anti-IgG and anti-IgM antibodies. After subtraction of the signal observed on the control plates adsorbed with BSA from that measured on the plates adsorbed with Tat101, no difference was observed between the signals obtained in the presence or absence of Tat101 as competitor, whatever the plasma dilution used (FIG. 2). These results demonstrate the absence of anti-Tat101 IgMs (FIG. 2A) or IgGs (FIG. 2B) in the plasmas and suggest that the corresponding blood contains B cells which are naïve with respect to Tat.

2.2 Preparation of Various Cell Subpopulations for the In Vitro Immunization

The capacity of Tat101 to induce antibody production was examined using three different cell populations. The PBMCs include all the mononuclear cells found in vivo. The NK-depleted PBMCs are free of the cells previously described as inhibiting the immune response in vitro. Finally, purified B lymphocytes were used for the purpose of studying the ability of Tat101 to induce antibody production in the absence of dendritic cells and of T-helper lymphocytes. The NK-depleted PBMCs were recovered from the PBMCs as nonretained cells after purification of the NK cells using anti-CD56 antibodies coupled to magnetic beads. The flow cytometry analysis (FIG. 3A) showed that the NK cells represented approximately 10% of the PBMCs before fractionation, while at most 0.42% of the NK cells remained after affinity chromatography, demonstrating a yield of more than 95% for this depletion step. An opposite procedure was used to purify the B lymphocytes. The affinity chromatography step involves anti-CD20 antibodies coupled to magnetic beads in order to specifically retain and purify the B lymphocytes. The flow cytometry analysis (FIG. 3B) showed that the B lymphocytes represented approximately 15% of the PBMCs, while the percentage of B lymphocytes reaches 98% after purification on magnetic beads.

2.3 In Vitro Immunization Experiments with Tat101 and ZZTat101

In order to compare the ability of free Tat101 or Tat101 fused to ZZ to trigger the production of specific antibodies in vitro, Tat101, ZZ, ZZTat101 and a mixture of ZZ and Tat101 were compared in the in vitro immunization experiments. Preliminary studies carried out in the presence or absence of 11-2, IL-4 and a ligand of TLR-9, CpG ODN 2006 (5'-TCGTCGTTTTGTCGTTTTGTCGTT-3'; SEQ ID NO: 7) showed that the cytokines/CpG cocktail conferred no benefit on the anti-Tat101 immune response. Consequently, all the experiments were carried out without cytokines and without CpG.

After incubation of various cell populations with the various antigens for 7 days at 37° C., the supernatants were harvested and analyzed using an ELISA in order to detect the Tat101-specific IgMs and IgGs. The analysis of the presence of anti-Tat101 IgMs in the supernatants from NK-depleted PBMCs (FIG. 4A) shows an absence of signal for the supernatants from the incubation with the free Tat101 protein or from the control incubation carried out in the absence of an antigen. The same results were observed when the IgG response was analyzed. These results demonstrate that the Tat101 protein is not capable of initiating an antibody response in vitro. This behavior changes when Tat101 is fused to ZZ, given that an IgM signal is observed in the supernatants resulting from the incubation with ZZTat101. This specific signal was not observed using Tat101 mixed with ZZ or ZZ alone, thereby showing that neither ZZ alone, nor a mixture of the two free proteins, is capable of triggering a specific IgM response.

All of these results show that only the covalent association of Tat101 and ZZ is capable of triggering a specific humoral response in vitro. The fact that no response is triggered when free Tat is incubated in the presence of ZZ indicates that the effect obtained is not linked to "bystander" mechanisms which could originate from the IgG binding domain. Furthermore, the phenomenon is not connected to the main biological activity of Tat, i.e. its transactivation activity, since ZZTat101 is devoid of transactivating activity (FIG. 1).

The antibody secretion was observed in the absence of cytokines which are normally used in in vitro immunization experiments. However, although anti-Tat IgMs were systematically observed, the presence of specific IgGs was found only in one experiment out of six. This suggests that ZZTat101, on its own, provides the signals required for triggering a primary immune response, but is not capable of inducing isotype switching.

Similar results were observed when the total PBMC fraction was used (FIG. 4B), indicating that NK cells do not modify the in vitro stimulation provided by ZZTat101. Consequently, the use of ZZTat101 makes it possible to do without the immunosuppressive-cell-depletion step normally used in in vitro immunization protocols, and therefore to simplify the in vitro immunization procedures without reducing the efficiency of the in vitro immunization.

The same behavior was also observed using purified B lymphocytes (FIG. 4C), suggesting that the in vitro stimulation induced by ZZTat101 does not require the presence of dendritic cells and of T-helper lymphocytes.

Furthermore, the genetic system used to produce ZZTat101, which allows the production of several antigens in tandem, is a useful tool for expressing other proteins linked to Tat, so as to provide the antigens incorporated with an in vitro stimulation capacity.

2.4 Determination of the Molecular Determinant, of the Fusion Protein, which is Involved in the Humoral Immune Response In Vitro A series of ZZTat101 derivatives was prepared in order to identify the molecular determinant, of the fusion protein, which is involved in the induction of a humoral immune response in vitro. The first, known as ZZTat22-57, comprises sequence 22-57 of Tat and the second, known as ZZTat22-57$_{C(22-37)S}$, corresponds to a mutant of ZZTat22-57 in which the seven cysteines of the cysteine-rich region (residues 22 to 37) have been replaced with serines. ZZTat101, ZZTat22-57 and ZZTat22-57$_{C(22-37)S}$ were incubated in the presence of NK cell-depleted-PBMCs in order to compare their capacity to trigger the humoral immune response in vitro. After 7 days of incubation, the supernatants were recovered and added to microplate wells preadsorbed with Tat101. In comparison with the supernatants of the incubation with ZZTat101, the supernatants of the incubation with ZZTat22-57 show a reduced IgM production. However, this production is greater than that observed with the control supernatants (FIG. 5), thereby indicating that region 22-57 of Tat triggers a significant immune response in vitro. Conversely, no response was observed with the supernatants resulting from the incubation with ZZTat22-57$_{C(22-37)S}$ which has an intact ZZ domain but is devoid of the seven cysteines of Tat, thereby indicating that, in the ZZTat101 fusion protein, it is the Tat protein which plays an essential role in the induction of the humoral immune response in vitro. These results also indicate that one or more of the cysteines of Tat contribute to this phenomenon. The capacity of ZZTat22-57 to trigger an immune response in vitro indicates that the molecular determinant is mainly located in region 22-57. Interestingly, the cysteine-rich region located between residues 22 and 37 is itself located inside the molecular determinant controlling the effect.

The analysis of ZZTat22-57$_{C(22-37)S}$, after separation by SDS-PAGE (FIG. 6), shows that, contrary to ZZTat22-57, which is capable of oligomerizing, ZZTat22-57$_{C(22-32)S}$, is incapable of oligomerizing. These results indicate that the capacity of ZZTat101 to induce a humoral immune response in vitro is related to the oligomerization properties of Tat, mediated by these cysteine residues.

EXAMPLE 3: THE IN VITRO INCUBATION OF PBMCS IN THE PRESENCE OF ZZ-TAT101 OR OF ZZ-TAT22-57 CAUSES THE SECRETION OF TAT-SPECIFIC IGGS

1. Materials and Methods
1.1 In Vitro Immunization

The residues of leukocyte/platelet concentrate from healthy donors (negative for HIV1/2, HTLV-I/II, HCV and HBsAg) originating from the Etablissement Français du Sang [French Blood Bank] (France) are deposited on ficoll (HISTOPAQUE®-1077, Sigma) and the PBMCs are isolated by density gradient centrifugation at 1200 g for 15 min. An osmotic lysis of the red blood cells is then carried out with 10 ml of lysis buffer (8.3 g NH$_4$Cl, 0.84 g NaHCO$_3$, 0.5 ml 0.2 M EDTA, qs 1l H$_2$O). After incubation for 10 minutes at 4° C., the cells are washed with 50 ml of PBS to which 2 mM EDTA have been added.

The cells are diluted in RPMI-1640 medium supplemented with 2 mM L-glutamine, penicillin (50 IU/ml), streptomycin (50 μg/ml), 50 μM β-mercaptoethanol and 10% of heat-inactivated fetal calf serum and deposited in 96-well plates in a proportion of 5×10$^5$ cells per well. The wells also contain the Ag (ZZ-Tat101, ZZ or ZZ+Tat101) at 10 μg/ml, an anti-CD40 antibody (1 μg/ml), IL-4 (10 ng/ml) and IL-21 (50 ng/ml). The mixtures are incubated at 37° C. and the supernatants are sampled 11 days later in order to evaluate the presence of Tat101-specific antibodies.

1.2 Assaying of the Abs in the Culture Supernatants

The presence of Tat-specific IgGs in the culture supernatants is evaluated by immunoenzymatic assay. Microtitration plates are adsorbed with the Tat protein (100 μl/well at 1 μg/ml in 0.1M phosphate buffer, pH 7.4). The wells are then saturated with a 0.1M phosphate buffer solution, pH 7.4, containing 0.3% of bovine serum albumin (BSA, 200 μl/well). After an overnight period at 4° C., the plates are washed and the supernatants diluted to ¼ are added to the wells (50 μl/well) in the presence or absence of various competitors. After an overnight period at 4° C., the wells are washed and a peroxidase-coupled anti-human IgG antibody is added to the wells. After incubation for 30 minutes, the plates are washed and 2,2'-azinobis[3-ethylbenzothiazoline-6-sulfonic acid] (ABTS) is added in order to reveal the enzymatic activity in the wells.

2 Results

In order to determine the capacity of free Tat101 or Tat101 coupled to ZZ to induce the immune response in vitro, it is essential to use PBMCs which are naïve with respect to this antigen. This selection was carried out on the basis of the absence of anti-Tat Abs in the plasmas from the residues of leukocytes/platelet concentrate containing PBMCs. The presence of Abs was evaluated using microtitration plates preadsorbed with Tat101 or with BSA. These plates were incubated with plasma dilution series, in the presence or absence of a solution of Tat101 (10 μg/ml). The interaction of the Abs with the plates was then measured by immunoenzymatic assay using anti-IgG and anti-IgM Ab. As can be seen in FIG. 7A, which represents the binding of the IgMs to the Tat101 plates, binding is measurable for plasma dilutions of ⅒, ¹⁄₁₀₀ and ¹⁄₁₀₀₀. However, this binding is not decreased in the presence of the excess of Tat101 in solution, thereby indicating that it is not specific for the protein. The same behavior is observed for the measurement of the IgG binding (FIG. 7B). These results therefore indicate that the plasmas tested are free of anti-Tat IgG and IgM antibodies and indicate that the blood bags contain B cells which are naïve with respect to Tat.

The leukocyte/platelet concentrate residues were then treated with a ficoll in order to recover the PBMCs. The capacity of Tat101 and ZZ-Tat101 to trigger the immune response in vitro was determined using PBMCs, an anti-CD40 antibody and two cytokines (IL-4 and IL-21) which contribute to the humoral immune response and also to isotype switching. The PBMCs and the cytokine mixture were incubated in the absence or presence of Tat101, ZZ-Tat101, ZZ, and ZZ+Tat, respectively. After various incubation times at 37° C., the supernatants were sampled and evaluated for the presence of Tat-specific IgGs. As can be seen in FIG. 8, the supernatants resulting from the incubation with ZZ-Tat101 contain IgGs capable of binding the microtitration wells that were preadsorbed with the Tat101 protein. On the other hand, the optical signal obtained with the supernatants resulted from the incubation with Tat101, ZZ or ZZ+Tat101 do not significantly differ from that measured for the supernatants resulting from the incubation of the PBMCs in the absence of Ag. These data therefore suggest that only the supernatants resulting from the incubation with ZZ-Tat101 contain Tat-specific IgGs. In order to determine whether the binding to the plates is actually Tat-specific, the inhibition of this binding was then evaluated in the presence of solutions containing either the Tat101 protein, or two unrelated Ags (ovalbumin, referred to as OVA, and lysozyme). As can be seen in FIG. 9, the binding is not significantly modified in the presence of OVA or of lysozyme, whereas it is completely abolished in the presence of the Tat101 solution, thereby demonstrating that the antibodies detected are Tat-specific. All of these results therefore indicate that the ZZ-Tat101 fusion protein is capable of triggering a humoral immune response in vitro and that the effect requires the covalent coupling of ZZ and Tat101.

In order to delimit the molecular determinant involved in the humoral immune response in vitro, two mutants of ZZ-Tat were prepared. The first, known as ZZTat22-57, was chosen since it comprises region 22-57 of Tat which contains the cysteine-rich (residues 22 to 37), core (residues 38 to 48) and basic (49 to 57) domains which are involved in numerous biological activities of Tat. The second corresponds to a mutant of ZZTat22-57 in which the 7 cysteine residues have been replaced with serines. ZZTat22-57 and ZZTat22-57$_{C(22-37)S}$ were incubated in the presence of PBMCs in order to compare their ability to trigger the immune response in vitro. After incubation for 11 days, the supernatants were collected and added to microtitration wells preadsorbed with Tat101. As can be seen in FIG. 10, the ZZTat22-57 supernatant exhibits binding to the plates which is greater than the binding with the supernatant resulting from the incubation with the control activation cocktail (anti-CD40/IL-4/IL-21), thereby indicating that the fusion protein including region 22-57 of Tat is capable of triggering the immune response in vitro. On the other hand, the supernatants resulting from the incubation with ZZTat22-57$_{C(22-37)S}$ do not bind more efficiently to the plates than the supernatants resulting from the incubation with the control activity cocktail (anti-CD40/IL- 4/IL-21). As can be seen in FIG. 11, the immune response induced by ZZTat22-57 is Tat-specific since two solutions containing, respectively, ovalbumin (OVA) and lysozyme are incapable of inhibiting the binding of the antibodies to the plates, whereas the solution containing Tat101 significantly decreases the IgG binding. The capacity to trigger the immune response in vitro depends on the ability to form oligomers mediated by the cysteines since, contrary to ZZTat22-27, which is capable of oligomerizing, ZZTat22-57$_{C(22-37)S}$ is incapable of oligomerizing (FIG. 6).

EXAMPLE 4: THE CAPACITY TO TRIGGER THE IMMUNE RESPONSE IN VITRO CAN BE GIVEN TO ANOTHER AG BY COVALENT COUPLING TO ZZ-TAT101

1. Materials and Methods
1.1. Coupling of Biotin to ZZ-Tat101
The ZZ-Tat101 protein (1 mg) is dissolved in 700 µl of 0.1M phosphate buffer, pH 7.5. The reactive biotin (2 mg of biotinamidocaproate N-hydroxysuccinimide ester) is dissolved in 100 µl of dimethylformamide. The solutions are mixed and incubated for 1 hour at room temperature with stirring. The reaction is stopped by adding glycine (200 µl diluted to 0.1M in 0.1M phosphate buffer, pH 7.5). The reaction mixture is then stored at −20° C. in lyophilized form. The coupling of the biotin to ZZ-Tat101 is evaluated by means of an immunoenzymatic assay test. In order to carry out these tests, microtitration plates are first of all adsorbed by incubation overnight at 4° C. with an rabbit IgG solution (100 µg/well at 1 µg/ml in 0.05M phosphate buffer, pH 7.2). The plates are then saturated by incubation overnight at 4° C. with a 0.1M phosphate buffer solution, pH 7.2, containing 0.3% of BSA (200 µl/well). The plates are then washed and dilutions of the reaction mixture are added. After incubation for 1 hour at roomtemperature, the plates are washed and the binding of ZZ-Tat101biot to the adsorbed IgGs is revealed using peroxidase-coupled streptavidin and ABTS as substrate.
1.2. In Vitro Immunization
The in vitro immunization experiments are carried out using a protocol similar to that described in example 2. The PBMCs and the activation mixture are incubated in the presence or absence of ZZTat101-biot. After 11 days at 37° C., the supernatants are sampled in order to evaluate the presence of biotin-specific antibodies.
1.3 Assaying of the Abs in the Culture Supernatants
The presence of biotin-specific IgGs in the culture supernatants is evaluated by immunoenzymatic assay. Microtitration plates are adsorbed with a peptide (100 µl/well at 1 µg/ml in 0.1M phosphate buffer, pH 7.4), known as Pri4Dbiot, which is unrelated to Tat and coupled to biotin. The wells are then saturated with a 0.1M phosphate buffer solution, pH 7.4, containing 0.3% of bovine serum albumin (200 µl/well). After an overnight period at 4° C., the plates are washed and the supernatants diluted to ¼ are added to the wells (50 µl/well) in the presence or absence of various competitors. After an overnight period at 4° C., the wells are washed and a peroxidase-coupled anti-human IgG antibody is added to the wells. After incubation for 30 minutes, the plates are washed and the ABTS is added in order to reveal the enzymatic activity of the wells.
2. Results
In order to evaluate whether the capacity of ZZ-Tat to trigger an IgG response in vitro can be transferred to other antigens, biotin was chosen given that it is a hapten incapable of triggering the immune response on its own. The biotin was chemically coupled to the ZZTat101 fusion protein in order to produce a ZZ-Tat-Ag compound, known as ZZ-Tat101-biot. PBMCs were then incubated under the culture conditions previously used for ZZ-Tat101 in the presence or absence of ZZ-Tat101-biot. After incubation for 11 days at 37° C., the supernatants were sampled in order to evaluate the presence of anti-biotin IgGs by immunoenzymatic assay. A signal was measured for the supernatants resulting from PBMCs incubated without Ag (FIG. 12). The signal is not, however, inhibited by a solution containing an excess of Pri4D-biotin peptide, thereby indicating that it corresponds to nonspecific binding to the plates. For the supernatants resulting from the incubation with ZZ-Tat101, a higher signal was measured. However, it is not significantly inhibited in the presence of the solution of Pri4Dbiot, thereby indicating that the binding to the plates is nonspecific. For the supernatants resulting from the incubation with ZZ-Tat101-biot, a higher signal that than observed for the supernatants resulting from the PBMCs incubated without Ag was measured. This signal is, furthermore, inhibited in the presence of the solution of Pri4D-biotin, thereby indicating that it corresponds to the binding of biotin-specific human IgGs. All of these results therefore demonstrate the capacity to trigger a humoral response and the production of specific human IgGs is conferred on the biotin when it is precoupled to ZZ-Tat101.

EXAMPLE 5: THE IN VITRO IMMUNIZATION ALLOWS INDUCTION OF B LYMPHOCYTES SECRETING IGGS SPECIFIC FOR THE AG INCLUDED IN THE FUSION PROTEIN

1. Materials and Methods
1.1 Synthesis of the NY-ESO-1 Peptide
A fragment of the NY-ESO-1 protein (SLLMWITQC-FLPVARGPESRLLEFYLAMPFATPMEAELARRSLA; SEQ: ID NO. 8) was chemically synthesized by means of the Fmoc/tert-butyl strategy using an Applied Biosystems 433A automatic peptide synthesizer. The chemical process uses 0.1 mmol of Fmoc-Asp(OtBu)-PAL-PEG-PS resin, a 10-fold excess of each amino acid, dicyclohexylcarbodiimide/1-hydroxy-7-azabenzotriazole and diisopropylethylamine/N-methylpyrrolidone. The cleavage and the deprotection are carried out using a trifluoroacetic acid/triisopropylsilane/water mixture (9.5/0.25/0.25, v/v/v). The crude material was precipitated twice with tert-butyl methyl ether, cooled to 4° C., then dissolved in an aqueous 15% acetic acid solution. The protein was then purified by reverse-phase high performance liquid chromatography (HPLC) on a Vydac C18 column (Hesperia). The peptides and the proteins synthesized were characterized by mass spectrometry and amino acid analysis. They are stored at −20° C., in lyophilized form.
1.2 Construction, Expression and Purification of the ZZ-NY-ESO-1-Tat Protein
The ZZ-NY-ESO-1-Tat fusion contains the NY-ESO-1 fragment and region 22-57 of Tat101 fused to ZZ. The synthetic nucleotide sequence SEQ ID NO: 5 encoding Tat101 peptide 22-57 is described in example 1. The NY-ESO-1 peptide is encoded by the nucleotide sequence: CTG CTG ATG TGG ATT ACC CAG TGC TTT CTG CCG GTG GCT CGT GGC CCG GAA AGC CGT CTG CTG GAA TTT TAC CTG GCG ATG CCG TTT GCG ACC CCG ATG GAA GCG GAA CTG GCG CGT CGT AGC CTG GCG (SEQ ID NO: 9). These two sequences were inserted into a vector pCP encoding the ZZ protein (Drevet et al., Protein Expression Purif., 1997, 10, 293-300), using the SacI/KpnI/BamHI restriction sites.

Bacteria (*E. coli* BL21de3) were then transformed with the plasmid. The fusion protein was expressed and then purified using an affinity column onto which antibodies (Abs) are grafted. The purity was evaluated by gel electrophoresis. The protein was produced with yields ranging between 1 and 5 mg/l of culture. It was stored in lyophilized form until use.

1.3 In Vitro Immunization

The in vitro immunization was carried out in 96-well plates by incubation of $5 \times 10^5$ PBMCs per well in the presence of an anti-CD40 antibody at 1 ng/ml, of IL-4 (10 ng/ml) and of IL-21 (50 ng/ml), and in the presence or absence of the ZZTat101 Ag or of the ZZ-NY-ESO-1-Tat Ag (concentration of 10 µg/ml for each fusion protein). The mixtures were incubated at 37° C. for 8, 11 or 13 days and then the presence of Tat-specific IgGs was evaluated by means of an ELISpot assay.

1.4. ELISpot Assay

The production of IgGs specific for Tat or for the NY-ESO-1 peptide by the B lymphocytes immunized in vitro was evaluated by ELISpot assay. ELISpot assay plates (Multiscreen™ Maha, Millipore™) were adsorbed with the Tat protein or with the NY-ESO-1 peptide (50 µl/well at 1 µg/ml in 50 mM carbonate buffer, pH 9.6). The wells were then saturated with RPMI-1640 containing 10% of heat-inactivated fetal calf serum (200 µl/well). After 2 hr at 37° C., the plates were washed and the PBMCs immunized in vitro were deposited (100 it of each in vitro immunization well/ELISpot plate well). After incubation for 24 h at 37° C., the plates were washed and a biotin-coupled anti-human-IgG antibody was added to the well. After incubation for 1 h 30 min at 20° C., the plates were washed and alkaline phosphatase-coupled streptavidin was added to the well. After incubation for 1 h at 20° C., the plates were washed and a mixture of BCIP (5-bromo-4-chloro-3-indolyl phosphate)/NBT (nitro blue tetrazolium; Promega) was added in order to reveal the enzymatic activity in the wells. The spots are visualized and counted on an ELISpot reader.

2. Results

In order to confirm that the in vitro immunization method of the invention allows the induction of B lymphocytes secreting IgGs specific for the Ag included in the fusion protein, PBMCs were incubated in culture plates with the cytokine cocktail for activation and in the presence or absence of ZZTat101. The mixture was then transferred into ELISpot plates preadsorbed with Tat. After incubation for 24 hours at 37° C., the plates were washed in order to remove the cells, and the presence of spots corresponding to the B lymphocytes capable of secreting Tat-specific-IgGs was revealed. As can be seen in FIG. 13 showing the number of Tat-specific spots as a function of incubation time of the PBMCs in the presence or absence of ZZTat, spots are measured in the wells containing the PBMCs and the activating cocktail only. However, after 8 and 11 days of incubation, this number of spots is significantly lower than that measured in the wells which also contained ZZTat. The behavior changes after 13 days of incubation. Indeed, the number of spots is no longer significantly different when the PBMCs are incubated with the activating cocktail, in the absence or presence of ZZTat. All of this data therefore indicate that the incubation of the fusion protein allows the induction of B lymphocytes capable of secreting anti-Tat IgGs with an optimum response which lies between day 8 and day 11.

In order to confirm that the in vitro immunization method of the invention allows the induction of B lymphocytes secreting IgGs specific for an Ag other than Tat, a fusion protein containing a fragment of the NY-ESO-1 protein, known as ZZ-NY-ESO-1-Tat, was used. PBMCs were incubated in culture plates with the cytokine cocktail for activation and in the presence or absence of two different concentrations of ZZ-NY-ESO-1-Tat or of ZZ-Tat. The mixture was then transferred into ELISpot plates preadsorbed with the NY-ESO-1 peptide. After incubation for 24 hours at 37° C., the plates were washed in order to remove the cells, and the presence of spots corresponding to the B lymphocytes capable of secreting NY-ESO-1-specific IgGs was revealed. As can be seen in FIG. 14, a small number of spots is counted when the PBMCs are incubated with ZZ-Tat. This number of spots is approximately five times lower than that measured when the PBMCs are incubated with ZZ-NY-ESO-1-Tat. This significant difference is found for the two protein concentrations that were used. All of these data therefore indicate that the incubation of ZZ-NY-ESO-1-Tat with the PBMCs allows the induction of B lymphocytes capable of secreting anti-NY-ESO-1 IgGs.

EXAMPLE 6: FUSION BETWEEN THE PBMCS INDUCED BY IN VITRO IMMUNIZATION AND THE CELLS OF A HUMAN/MURINE HETEROMYELOMA RESULTS IN THE PRODUCTION OF B HYBRIDOMAS CAPABLE OF SECRETING TAT-SPECIFIC IGGS

1. Materials and Methods 1.1. In Vitro Immunization of PBMCs Before the Cell Fusion Step The in vitro immunization of the PBMCs was carried out in Petri dishes in a proportion of $25 \times 10^6$ cells per dish in a final volume of 15 ml of medium (RPMI-1640 supplemented with L-glutamine (2 mM), sodium pyruvate (1 mM), penicillin (50 IU/ml), streptomycin (50 µg/ml) and 10% of heat-inactivated fetal calf serum). The various cell populations were incubated in vitro in the presence of the ZZTat101 Ag at 10 µg/ml, of an anti-CD40 antibody at 1 ng/ml, of IL-4 at 10 ng/ml and of IL-21 at 50 ng/ml. The mixtures were incubated at 37° C. for 11 days and then the cells were isolated with a view to the cell fusion step.

1.2. Culturing of the Human/Murine Heteromyeloma (HM) Cells Before the Cell Fusion Step The human/murine heteromyeloma cells are cultured in RPMI-1640 medium supplemented with 2 mM L-glutamine, 1 mM sodium pyruvate, penicillin (50 IU/ml), streptomycin (50 µg/ml) and 10% of heat-inactivated fetal calf serum.

1.3. Cell Fusion

The PBMCs immunized in vitro ($4 \times 10^7$ cells) were mixed with the heteromyeloma cells ($2 \times 10^7$ cells) in RPMI-1640 medium and then the cell mixture was centrifuged (10 minutes at 1000 rpm). The cell fusion was carried out by means of the dropwise addition of the fusing agent, 50% polyethylene glycol (PEG 400, Sigma Aldrich). The cells were then washed, taken up in selected medium (RPMI-1640 supplemented with 2 mM L-glutamine, 1 mM sodium pyruvate, 1% amino acids, penicillin (50 IU/ml), streptomycin (50 µg/ml), 20% of heat-inactivated fetal calf serum) supplemented with hypoxanthine (0.1 mM), aminopterin (0.4 mM) and thymidine (16 mM), and then deposited in 96-well plates (100 µl/well).

1.4. Selection of the Hybridomas Producing Tat-Specific IgGs

Immunoenzymatic assay plates were prepared. In these plates, the Tat protein (100 μl/well at 1 μg/ml in 0.1M phosphate buffer, pH 7.4) was incubated overnight at 4° C. in the microtitration plates. The wells were then saturated with a 0.1M phosphate buffer solution, pH 7.4, containing 0.3% of bovine serum albumin (BAS, 200 μl/well). After an overnight period at 4° C., the plates were washed and then culture supernatants from each well containing the fused cells were diluted to ¹/₁₀ and added to these plates (100 μl/well). After an overnight period at 4° C., the plates were washed and a peroxidase-coupled anti-human IgG antibody was added to the wells. After incubation for 30 minutes, the plates were washed and 2,2'-azinobis[3-ethylbenzothiazoline-6-sulfonic acid] (ABTS) was added in order to reveal the enzymatic activity in the wells. The threshold value used to identify the wells containing hybridomas secreting Tat-specific IgGs corresponds to the average optical density of the eight wells containing only HM plus three standard deviations (the standard deviation is defined on the basis of the signals obtained for the eight wells containing only HM).

2. Results

Experiments involving cell fusion with a human/murine heteromyeloma (HM) were carried out in order to evaluate whether the PBMCs induced by in vitro immunization can be immortalized and can produce IgGs specific for the Ag included in the fusion protein. In these experiments, PBMCs induced by in vitro immunization with ZZTat101 were incubated in the presence of HM and of PEG400. Following this fusion, the cells were distributed into wells of a microtitration plate in the presence of a selected medium which makes it possible to eliminate the non-fused heteromyeloma. The supernatants contained in the wells were then sampled and the presence of Tat-specific IgGs was measured by immunoenzymatic assay. The results are presented in tables I and II.

TABLE I

ELISA assays of anti-Tat IgGs in the hybridoma supernatants

| TAT 1 | 1 | 2 | 3 | 4 | 5 | 6 | 7 | 8 | 9 | 10 | 11 | HM alone 12 |
|---|---|---|---|---|---|---|---|---|---|---|---|---|
| A | 0.058 | 0.039 | 0.036 | 0.052 | 0.042 | 0.042 | 0.045 | 0.037 | 0.051 | 0.048 | 0.05 | 0.091 |
| B | 0.022 | 0.01 | 0.018 | 0.024 | 0.032 | 0.079 | 0.071 | 0.065 | 0.062 | 0.053 | 0.028 | 0.056 |
| C | 0.022 | 0.015 | 0.043 | 0.065 | 0.055 | 0.123 | 0.165 | 0.183 | 0.116 | 0.035 | 0.031 | 0.041 |
| D | 0.017 | 0.028 | 0.047 | 0.086 | 0.165 | 0.1 | 0.083 | 0.079 | 0.035 | 0.024 | 0.037 | 0.031 |
| E | 0.012 | 0.012 | 0.017 | 0.042 | 0.054 | 0.055 | 0.027 | 0.014 | 0.012 | 0.019 | 0.015 | 0.021 |
| F | 0.017 | 0.007 | 0.026 | 0.009 | 0.006 | 0.008 | 0.011 | 0.011 | 0.011 | 0.011 | 0.01 | 0.023 |
| G | 0.03 | 0.012 | 0.015 | 0.008 | 0.006 | 0.009 | 0.008 | 0.003 | 0.01 | 0.007 | 0.012 | 0.04 |
| H | 0.058 | 0.036 | 0.031 | 0.032 | 0.044 | 0.034 | 0.033 | 0.022 | 0.044 | 0.034 | 0.047 | 0.063 |

TABLE II

ELISA assays of anti-Tat IgGs in the hybridoma supernatants

| TAT 3 | 1 | 2 | 3 | 4 | 5 | 6 | 7 | 8 | 9 | 10 | 11 | 12 |
|---|---|---|---|---|---|---|---|---|---|---|---|---|
| A | 0.032 | 0.023 | 0.013 | 0.022 | 0.059 | 0.019 | 0.021 | 0.02 | 0.032 | 0.038 | 0.036 | 0.052 |
| B | 0.033 | 0.007 | 0.002 | 0.004 | 0.008 | 0.011 | 0.032 | 0.047 | 0.06 | 0.037 | 0.004 | 0.031 |
| C | 0.015 | 0.017 | 0.059 | 0.041 | 0.097 | 0.115 | 0.136 | 0.092 | 0.048 | 0.098 | 0.036 | 0.031 |
| D | 0.013 | 0.135 | 0.043 | 0.111 | 0.199 | 0.088 | 0.178 | 0.185 | 0.174 | 0.127 | 0.036 | 0.026 |
| E | 0.016 | 0.105 | 0.064 | 0.091 | .145 | 0.114 | 0.065 | 0.162 | 0.128 | 0.056 | 0.009 | 0.019 |
| F | 0.021 | 0 | −0.005 | −0.003 | −0.006 | 0.006 | 0.011 | 0.017 | 0.007 | 0.029 | −0.002 | 0.018 |
| G | 0.027 | 0.001 | −0.003 | −0.002 | −0.005 | −0.005 | −0.004 | −0.003 | −0.004 | 0.021 | 0.001 | 0.019 |
| H | 0.049 | 0.028 | 0.02 | 0.023 | 0.016 | 0.021 | 0.024 | 0.023 | 0.023 | 0.021 | 0.034 | 0.044 |

As can be seen in tables I and II, five wells are positive in the plate called Tat1, while ten wells are positive in the plate called Tat3. These data therefore indicate that the fusion between the PBMCs induced by in vitro immunization with ZZTat101 and the cells of a human/murine heteromyeloma results in the production of 15 B hybridomas capable of secreting Tat-specific IgGs.

The invention claimed is:

1. A method for the in vitro immunization of human B lymphocytes, comprising culturing a total population of human peripheral blood mononuclear cells in the presence of an antigenic composition comprising at least one antigen covalently bonded both to: (i) a Tat protein or a Tat fragment capable of oligomerizing and (ii) a ligand of a surface molecule specific for antigen-presenting cells selected from the group consisting of: a BB protein, a ZZ protein, an anti-MHC class II, anti-FcgammaR, anti-IgM, anti-IgD, anti-IgG, anti-DEC-205, anti-CD209 or anti-CD20 antibody, and a fragment of the above antibodies comprising at least the paratope.

2. The in vitro immunization method as claimed in claim 1, wherein said surface molecule specific for antigen-presenting cells is selected from the group consisting of: membrane immunoglobulins, IgGs interacting with immunoglobulin constant region receptors, immunoglobulin constant region receptors, MHC class II molecules, CD20 and C-type lectin receptors.

3. The in vitro immunization method as claimed in claim 1, wherein said Tat protein or said Tat fragment oligomerizes by means of a cysteine or cysteines of the cysteine-rich region.

4. The in vitro immunization method as claimed in claim 1, wherein said Tat fragment comprises the cysteine-rich, core and basic regions.

5. The in vitro immunization method as claimed in claim 1, wherein said Tat fragment is chosen from the Tat 22-57 peptide and variants of said peptide which have one to six of the cysteines corresponding to C22, C25, C27, C30, C31, C34 and C37 of SEQ ID NO. 3, and the remaining cysteines of the sequence of the peptide being replaced with another amino acid.

6. The in vitro immunization method as claimed in claim 1, wherein said antigenic composition comprises at least the antigen covalently bonded to a fusion protein between a ZZ protein and a Tat protein or a Tat fragment chosen from the Tat 22-57 peptide and variants of said peptide which have one to six of the cysteines corresponding to C22, C25, C27, C30, C31, C34 and C37 of SEQ ID NO. 3, and the remaining cysteines of the sequence of the peptide being replaced with another amino acid.

7. The in vitro immunization method as claimed in claim 6, wherein said composition also comprises an anti-MHC class II antibody, an anti-FcgammaR, antibody, an anti-IgD antibody, an anti-IgM antibody, an anti-IgG antibody, an anti-DEC-205 antibody, an anti-CD209 antibody or an anti-CD20 antibody, bound noncovalently to said ZZ protein.

8. The in vitro immunization method as claimed in claim 1, wherein said antigen is a target for the diagnosis or treatment of a disease.

9. The in vitro immunization method as claimed in claim 8, wherein said disease is chosen from cancers, autoimmune diseases, diseases caused by pathogenic agents and toxins thereof, chronic inflammatory diseases, and graft rejection.

10. The in vitro immunization method as claimed in claim 1, wherein said antigenic composition comprises at least one B lymphocytes activation factor and/or one B lymphocytes differentiation factor.

11. A method for producing antigen-specific human antibodies, comprising:
  a) the in vitro immunization of human B lymphocytes with an antigen according to the in vitro immunization method of claim 1,
  b) the immortalization of the immunized B lymphocytes obtained in step a), and c) the recovery of the antigen-specific human antibodies produced by the immortalized B lymphocytes obtained in step b).

12. The antibody production method as claimed in claim 11, comprising an additional step of cloning the immortalized B lymphocytes, between steps b) and c).

13. The antibody production method as claimed in claim 11, wherein said antigen-specific antibodies are human antibodies of IgG isotype.

14. The antibody production method as claimed in claim 11, wherein said antigen-specific antibodies are human monoclonal antibodies.

* * * * *